United States Patent [19]

Carpenter et al.

[11] Patent Number: 4,473,647

[45] Date of Patent: Sep. 25, 1984

[54] TISSUE CULTURE MEDIUM

[75] Inventors: Charles R. Carpenter; Robert O. Cone, Jr., both of Seguin, Tex.

[73] Assignee: AMF Inc., White Plains, N.Y.

[21] Appl. No.: 349,691

[22] Filed: Feb. 17, 1982

Related U.S. Application Data

[63] Continuation-in-part of Ser. No. 238,686, Feb. 27, 1981, abandoned.

[51] Int. Cl.³ .................. C12N 5/00; C12N 1/38; A61K 35/16; C07G 7/00
[52] U.S. Cl. ............................. 435/240; 435/244; 424/101; 260/112 B
[58] Field of Search ............ 435/240, 241, 243, 244, 435/948; 424/101; 260/112 B

[56] References Cited

U.S. PATENT DOCUMENTS

| | | | |
|---|---|---|---|
| 3,122,476 | 2/1964 | Gaeta | 435/240 |
| 3,128,228 | 4/1964 | Michl | 435/240 |
| 3,429,867 | 2/1969 | Bozicevich | 435/240 |
| 3,686,395 | 8/1972 | Stephen | 424/101 |
| 4,007,008 | 2/1977 | Becker et al. | 436/16 |
| 4,038,139 | 7/1977 | Birch | 435/240 |
| 4,059,512 | 11/1977 | Harris | 424/101 |
| 4,081,431 | 3/1978 | Stephan et al. | 424/101 |
| 4,136,094 | 1/1979 | Condie | 424/101 |

OTHER PUBLICATIONS

Biocell Laboratories Catalog (5 pp.).
Todaro and Green, Proceedings of the Society of Experimental Biology and Medicine, vol. 116, p. 688, (1964).
Lieberman and Ove, Journal of Biological Chemistry, vol. 223, p. 637 (1958).
Holmes and Wolfe, Journal of Biophysical and Biochemical Cytology, 10:389 (1961).
Fisher et al., Biochemistry, vol. 102, p. 213, (1959).
Chang et al., Proceedings of the Study of Experimental Biology and Medicine, vol. 102, p. 213, (1959).
Jacquez and Barry, "Tissue Culture Media", pp. 765–773, (1951).
Kent and Gey, Proceedings of the Society of Experimental Biology and Medicine, vol. 94, pp. 205–208, (1957).
Fisher et al., Journal of Experimental Medicine, vol. 109, p. 649, (1959).
Fisher et al., Proceedings of the National Academy of Sciences, vol. 44, p. 4, (1958).
Puck et al., Proceedings of the National Academy of Sciences, vol. 59, p. 192, (1968).
Sato et al., Science, vol. 126, p. 961, (1957).
Ham, Methods in Enzymology, vol. 43, pp. 44–93, (1979).
Rothblat et al., "Growth, Nutrition and Metabolism of Cells in Culture", vol. I, Academic Press (1972), pp. 303–306.
Tombaccini et al., "Lipid Composition of Balb/c3T3, SV3T3, and Concanavalin, A Selected Revertant Cells Grown in Media Containing . . . ", Journal of Lipid Research, 22(4), (1981), pp. 590–597, Chem. Abst., 95:40533u.

*Primary Examiner*—Thomas G. Wiseman
*Assistant Examiner*—John E. Tarcza
*Attorney, Agent, or Firm*—David E. Dougherty; Michael E. Zall

[57] ABSTRACT

A natural bovine serum-derived serum which has low lipid levels and may additionally have similar globulin and albumin profile as fetal calf serum, as well as controlled levels of hemoglobin, enveloped viruses, steroid hormones, mycoplasma, cholesterol, triglycerides and pesticides, is useful for the promotion of growth of animal and plant cells in tissue culture.

32 Claims, 11 Drawing Figures

TISSUE CULTURE MEDIUM

BACKGROUND OF THE INVENTION

This is a continuation-in-part of application Ser. No. 238,686 filed Feb. 27, 1981, now abandoned.

1. Field of the Invention

The present invention relates to tissue culture media useful for the in vitro growth of cells.

2. Description of the Prior Art

It is well known that animal and plant cells may be grown in vitro in liquid culture media, i.e., tissue culture; see e.g. Kruse et al, Academic Press, New York, N.Y., 1973, and Ham, R. G. and McKeehan, W. L., Methods in Enzymology, 43:44–93(1979). Such media usually contain a wide array of different components, including various nutrients and salts which promote the maximum growth of the cultured cells.

Cells grown in tissue culture are used for many different purposes; for example, for the production of enzymes, cell products, antibodies, or for the general testing of drugs, carcinogenic agents and the like. In vitro growth of animal cell lines has recently acquired new relevance with the development of cell fusion, and the preparation of hybridomas and their associated monoclonal antibodies.

The art has long established that one of the essential components for tissue culture media is bovine serum, most preferably fetal calf or newborn calf serum. These two types of serum lack high concentrations of components which inhibit cell growth, and contain undefined factors which support cell growth in vitro. The use of fetal calf serum however, is troubled by a lack of sufficient supply, and poor characterization of its ingredients. Furthermore, costs for this type of serum have prevented the economic growth of cells containing such serum.

A number of fetal calf serum substitutes have been proposed. For example, Michl, U.S. Pat. No. 3,128,228 discloses a culture medium for the preparation of tissue cultures on the basis of serum protein fractions, and a nutrient solution containing nutrient salts, protein fission products, and particular amino acids, further sugars and vitamins or coenzymes. The serum substitute is derived from calf blood by coagulation, isolation of the serum, followed by a series of precipitation steps thereon.

Bozicevich, U.S. Pat. No. 3,429,867 describes a so-called "Agamma" calf serum suitable for tissue cultures, prepared from calf serum by precipitation and acidification thereon.

Birch, U.S. Pat. No. 4,038,139 describes a culture medium containing swine serum and about 0.1% of a surfactant which inhibits the precipitation of protein. The swine serum of Birch is stated to support the growth of lymphoid cells giving superior yields to those obtained using fetal calf serum. Swine serum is also considerably less expensive and thus brings about a concomitant reduction in cost.

Gaeta, U.S. Pat. No. 3,122,476 describes a substitute fetal calf serum useful for the growth of normal human cells and other animal cells in vitro, prepared from the blood of immature calves by fractionation, isolation of the serum and separation therefrom of gamma-globulins and other toxic substances, by ethyl alcohol precipitation.

The difficulties with one or more of these prior art sera is that extensive and unselective precipitation by salt, acid or organic solvents causes the removal of essential growth factors which render the resulting substitute sera effective for only relative short periods of time, i.e., some of these sera are unable to support cell growth over many generations. Furthermore, it is well known that calf serum contains a number of toxins not present in fetal calf serum, which toxins tends to inhibit cell growth. An additional disadvantage encountered in some of these sera is the lack of complete standardization of components, which would provide controllable conditions for cell growth in tissue cultures.

A need therefore continues to exist for a standardized, well characterized fetal calf serum-substitute derived from calf serum, which contains active growth ingredients and lacks cell growth inhibiting toxins.

SUMMARY OF THE INVENTION

It is therefore an object of the invention to provide a highly efficient tissue culture medium derived from calf serum.

It is another object of the invention to provide a tissue culture medium which is well characterized and will permit controlled growth of animal and plant cells in vitro.

Yet another object of the invention is to provide a process for the production of a tissue culture medium.

Still another object of the invention is to provide a method for the growth of animal and plant cells in vitro, by utilizing the culture medium of the invention.

These and other objects of the invention as will hereinafter become more readily apparent have been attained by providing a natural bovine serum-derived serum which has low lipid levels and may additionally have similar globulin and albumin profile as fetal calf serum, as well as controlled levels of hemoglobin, enveloped viruses, steroid hormones, mycoplasma, cholesterol, triglycerides and pesticides. The serum comprises less than 30 mg/dl of total lipid concentration; cholesterol levels within 0–10 mg/dl; triglyceride levels within 0–15 mg/dl; hemoglobin levels less than 20 mg/dl; mycoplasma and enveloped viruses levels being substantially undetectable.

These objects have also been attained by providing a process for the production of a serum which comprises delipidizing natural bovine serum to a concentration of lipids less than 30 mg/dl. This process also reduces hemoglobin, mycoplasma and endogenous bovine viruses.

These objects have also been attained by providing a method for the growth of animal and plant cells in vitro which comprises culturing said cells in the presence of the aforementioned serum when complemented with fetal calf serum ("spiked" serum).

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
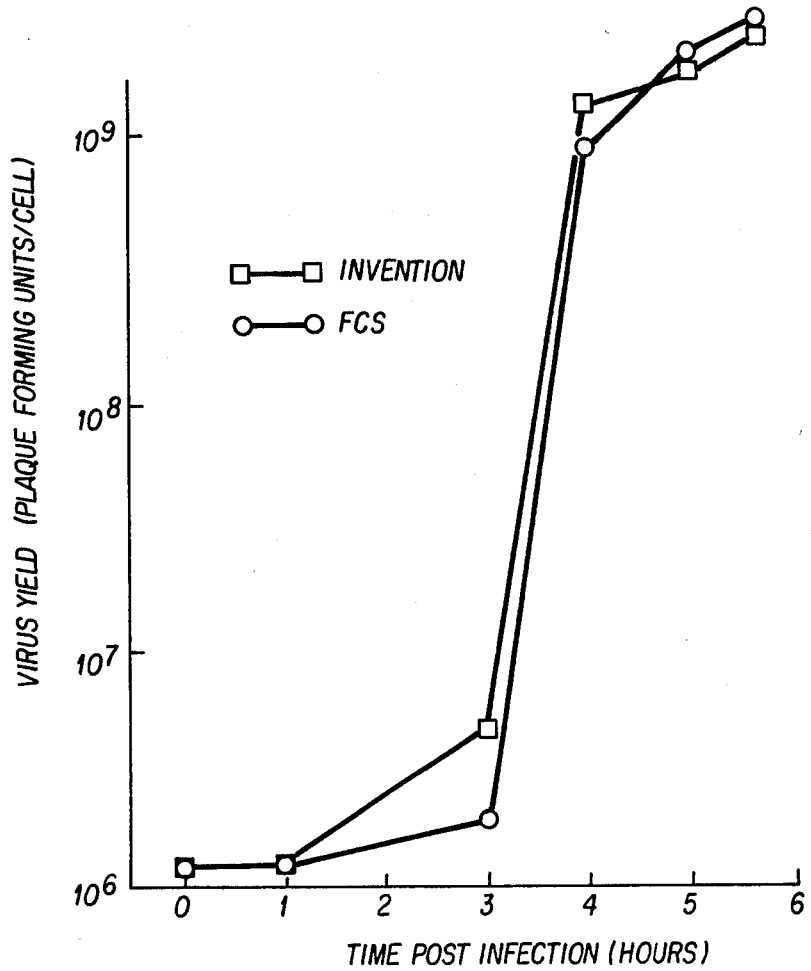
FIG. 1 compares the growth of VSV in mouse cells adapted to Fetal Calf Serum (FCS - Reheis ®) and to serum of the invention ("Zeta" serum). See Example 8.

The present inventors have discovered that if natural bovine sera are treated to delipidize the same and to remove endotoxin therefrom, as well as other toxins, steroids, gamma-globulins, infections agents and small molecular weight compounds, the resulting low lipid sera are highly useful intermediate for the preparation of substitutes for fetal calf sera, during the culturing of animal and plant cells in vitro. The low lipid, low steroid, low gamma-globulin sera of the invention have low toxicity towards such cells, and when complemented with fetal calf serum allow controlled culture of such cells, for extended periods of time.

The term "lipids" as used in this invention includes generally the alcohol and ether soluble constituents of serum which are insoluble in water. They comprise the fats, fatty acids, fatty oils, essential oils, waxes, steroids, phospholipids, glycolipids, sulfolipids, aminolipids, and chromolipids (lipochromes). The term also includes lipoproteins, triglycerides, as well as the lipid containing envelopes and membranes of mycoplasma.

The term "endotoxin", also known in the art as "bacterial pyrogen", as used in this invention, refers to the heat stable toxins present in the bacterial cell but not in propagating cultures of intact bacteria, and which are usually released from said bacteria by autolysis upon bacterial cell death. Endotoxins are found primarily in enteric bacilli, but are also found in certain of the gram negative cocci. Endotoxins are pyrogenic, increase capillary permeability, and have profound effects on cell growth, particularly lymphoid cells. The activity is substantially the same regardless of the species of bacteria from which they are derived.

The term "pesticide" includes normally occurring chlorinated pesticides and organophosphate pesticides of various types, such as $\alpha$ and $\beta$ isomers of 1, 2, 3, 4, 5, 6, hexachlorocyclohexane, aldrin or TDE (tetrachlorodiphenylethane).

The unspiked sera of the invention contain less than 30 mg/dl of total lipids, preferably less than 10 mg/dl, most preferably as close as possible to 0 mg/dl total lipids. It is generally known in the art that high lipid levels are undesirable. In this invention, however, lipid levels have been decreased even below those of fetal calf serum.

In addition to the characteristics of having low lipid levels generally, the sera of the present invention has the following biochemical features:

(a) Cholesterol is in the range of 0–10 mg/dl preferably 0–2 mg/dl;

(b) Triglycerides are in the range of 0–20 mg/dl, preferably 0–5 mg/dl;

(c) Enveloped bovine viruses such as PI-3, IBR and BVD are present in substantially undetectable amounts, as measured by the assay described in Molander, C. W. et al, In Vitro, 7:168–173 (1972), herein incorporated by reference.

(d) Mycoplasma is present in substantially undetectable amounts, as measured by the assay described in Barile, M. F. et al, Proc. Soc. Exp. Biol. Med. 138:432–437 (1971), herein incorporated by reference.

(e) Hemoglobin levels in the sera of the invention is less than 20 mg/dl; preferably less than 5 mg/dl;

In addition to these characteristics, the sera may also have the following features:

(f) The preferred electrophoretic profile for protein content of the sera of the invention may show albumin, alpha globulin and beta globulin in levels substantially similar to those of fetal bovine serum, although alpha globulin levels usually run at somewhat lower levels. While adult or most newborn calf serum contains gamma-globulin, fetal bovine serum does not contain any significant amounts. The fetal bovine serum substitute of the present invention may contain very low levels of gamma-globulin, brought about by removal thereof from the starting material, during the process of preparation. Total protein in the sera of the invention may be in the range of 3–7 g/dl. Albumin may vary between 2 and 4 g/dl. Alpha globulin may be in the range of 2.0–0.4 g/dl. Beta globulin may be in the range of 2.0–0.4 g/dl. Gamma-globulin may be in the range of 0.1–1.0 g/dl; preferably 0.0–0.5 g/dl;

(g) The ranges of endotoxin in the sera of the present invention may be less than 2.0 ng/ml, preferably less than 0.3 ng/ml, most preferably less than 0.1 mg/ml;

(h) Enzyme levels in the sera of the invention are generally within the normal ranges of fetal bovine serum. Thus alkaline phosphatase can be in the range of 100–300 mu/ml; GGT ($\gamma$-glutamyl transpetidase) 10–30 mu/ml; SGOT (serum glutamic oxaloacetic transaminase) 10–80 mu/ml. LDH (lactate dehydrogenase) levels will depend on the age of the calf, and are preferably within the normal range of fetal bovine serum (200–600 mu/ml). However, higher levels of LDH (up to 2500 mu/ml) do not harm the growth promoting properties of the sera of the invention;

(i) Insecticide levels, such as the $\alpha$ isomer of 1, 2, 3, 4, 5, 6, hexachloro cyclohexane ($\alpha$-BHC) is less than 0.15 pt/million; $\beta$-BHC is less than 0.05 pt/million; $\gamma$-BHC is less than 0.15 pt/million; aldrin is less than 1.5 pt/million; TDE less than 0.6 pt/million;

(j) Heavy metals as well as electrolytes are readily controlled during the processing and their values are given below in Table 1;

(k) Uric acid levels may be less than 2 mg/dl, preferably less than 0.5 mg/dl;

(l) Cortisol levels may be less than 5 μg/dl, preferably less than 1 μg/dl. Cortisol is representative of steroid hormones.

Table 1 compares the ranges of biochemical components of the unspiked sera of the invention, including preferred sera, (a) with similar components present in natural sera from donor calves less than 1 year old, (b) with natural sera from newborn calves (two sources), and (c) with natural sera from fetal calves. The Table demonstrates that total lipid levels including cholesterol and triglycerides levels are particularly low in the unspiked sera of the present invention and distinguish the sera of the invention from the corresponding natural products. Other biochemical ingredients also serve to further distinguish the sera of the invention. In some cases (i.e. enzymes) the normal values reflect parameters that are intentionally left unmodified in the sera of the invention.

tion as well as any other process steps which serve to further refine the product.

Delipidization of the unspiked serum can be carried out with any well-known delipidization method or agent therefor, such as for example, silica, hydrophobic interactions, polyanionic compounds such as dextran sulfate, freezethaw followed by filtration, etc.

A preferred method is the treatment of serum with fumed silica, (see e.g. Stephan, U.S. Pat. No. 3,686,395) either in batch form or by using immobilized fumed silica. The immobilization of fumed silica in fibrous media is fully described in commonly assigned copending U.S. patent application Ser. No. 347,360, filed Feb. 9, 1982 to Hou for FIBROUS MEDIA CONTAINING MILLIMICRON-SIZED PARTICLES. This application, which is herein fully incorporated by reference, describes a method of immobilizing fumed silica in a fibrous matrix by vacuum felting to a sheet a slurry

TABLE 1

| Profile | Serum of Invention | Donor Calf[1] Serum | Newborn Calf[2] Serum | Fetal Calf Serum |
|---|---|---|---|---|
| Total Lipids mg/dl | ≦30 | 400[4] | 300 | ~ 300 |
| Total Protein | | | | |
| Content g/dl | 3–7 | ~ 6 | ~ 4–5 | ~ 3.5 |
| Albumin g/dl | 2–4 | ~ 2.5 | ~ 2.2 | ~ 3.5 |
| α - Globulin g/dl | 0.4–2.0 | ~ 1.0 | ~ 1.0 | ~ 1.0 |
| β - Globulin g/dl | 0.4–2.0 | ~ 0.7 | ~ 0.75 | ~ 0.4 |
| γ - Globulin g/dl | 0.1–1.0 | ~ 1.5 | ~ 0.7 | — |
| Cholesterol mg/dl | 0–10 | ~ 80 | ~ 60 | ~ 25 |
| Triglycerides mg/dl | 0–20 | ~ 35 | ~ 22 | ~ 23 |
| Hemoglobin mg/dl | ≦20 | ~ 25 | ~ 35 | ~ 60 |
| Uric Acid mg/dl | ≦0.2 | ~ .2 | ~ .8 | ~ 2.5 |
| Cortisol μg/dl | ≦4 | ~ 15 | ND[5] | ~ 0.4 |
| Enzymes | | | | |
| Alkaline Phosphatase | 100–300 | ~ 100 | ~ 200 | ~ 230 |
| GGT mu/ml | 10–30 | ~ 30 | ~ 260 | ~ 16 |
| SGOT mu/ml | 30–80 | ~ 1 | ~ 20 | ~ 50 |

[1]Commercially available from Flow Inc.
[2]Commercially available from Flow Inc.
[3]Commercially available from KC Biol. Inc.
[4]The values given may range to ± 10%
[5]Not determined.

The process for the production of one or more of the unspiked sera of the invention comprises delipidizing natural bovine serum, while also removing from said serum mycoplasma, hemoglobin, as well as steroids, viruses, gamma-globulins, and small MW compounds, to the concentration levels specified previously.

The preparation of bovine serum from bovine blood is generally well known in the art and will not be described in great detail. Any process of preparing serum from calf blood is useful to prepare the sera of the invention.

Calves, preferably feedlot calves of either sex, either grain fed or grass fed, preferably grain fed and preferably being less than 1 year old are bled according to standard practice in the art. Serum from feedlot calves has heretofore been considered unuseable for tissue culture media, due to the usual condition of hyperlipidemia in such calves. This hyperlipidemia normally raises lipid levels in the blood. This invention, however, has surprisingly made use of this heretofore believed unusable serum source.

Red blood cells are separated from the blood, for example, by centrifugation. The supernatant plasma is clotted, as for example by addition of bovine thrombin and calcium. Alternatively, blood is simply allowed to clot. The serum is separated by filtration or centrifugation from the clotted blood, and is ready for delipidizacontaining fumed silica, fibers, as well as a polycationic and polyanionic resin in amounts sufficient to flocculate the fumed silica. With such immobilized fumed silica it becomes possible to simply contact serum with the fumed silica-containing sheets, and achieve the results of the present invention. For example, the fibrous media in the form of sheets can be cut in discs. These discs can be stacked in a cylindrical column and the serum to be treated is then flowed through the column. If the discs in the column contain at least delipidizing amounts of fumed silica (or excess of fumed silica), the column will constitute an efficient, fast and economical apparatus for delipidization. Such method is now preferred over the batch treatment, since it avoids the use of free silica powder with its accompanying problems of dust, separation, clarification of the product serum, and the like.

When the silica treatment is carried out in batch form, it is possible to add fumed silica to the serum directly. The silica useful in the invention can be any of those commercially available, especially those sold as Aerosil ® or Cab-O-Sil ®. The surface area and particle size of the silica can vary broadly, embracing sizes of 1 to 50 m and densities of 2.5 to up to 7.8 lbs/ft$^3$. Especially effective are the silicas having high surface areas, preferably higher than 300 sq. m/gm, although any product having a value within the range of 50 to 400 sq. m/gm can be used. The silica is added at 10–100 g/l of serum, most preferably at 20–30 g/l of serum. In batch treatment, the fumed silica is stirred at from 0° C. to room temperature for 1 hour–48 hours preferably 4–8 hours.

It is beneficial, when carrying out the delipidization with fumed silica to add to the serum, just prior to the treatment with silica, a divalent metal ion such as calcium, magnesium, or manganese, to a concentration range of 0.01–0.5M preferably to a value of 0.05M. The addition of the divalent metal ion presumably functions to aide the delipidization process with silica. If the silica treatment step is carried out immediately after clotting in the presence of $Ca^{+2}$, the divalent metal ion is already present. When working in the batch mode, separation of the lipid-containing fumed silica from the remaining delipidized serum can be carried out by any of the well known physical methods of separation, such as centrifugation, filtration, decantation, and the like. In the continuous column mode, no such separation is, of course, needed. Lipid levels can be followed by colorimetric enzymatic assay.

Silica treatment is not only capable of removing lipids (including cholesterol and triglycerides), but also serves to decrease the levels of hemoglobin to less than 20 mg/dl, and serves to remove any enveloped viruses and mycoplasma.

Removal of endotoxin, a peptide having a molecular weight normally less than 10,000, can be carried out by any process capable of removing low molecular weight materials from serum. Such process may include but is not limited to diafiltration, dialysis, gel filtration chromatography, ultrafiltration and the like. The most preferred method due to its fastness and efficiency is diafiltration using commercially available hollow filter devices with 10,000 MW cutoff filters. Diafiltration can be carried out with serum at a pH range of from 5 to 9, at temperatures from 0° C. to room temperature, with any physiological buffers systems, such as: HEPES, Tris, glycerolphosphate, PIPES, imidazole, carbonate, acetate and the like. Preferred buffer is acetate or carbonate. The number of buffer changes can be routinely adjusted until the desired level of endotoxin is achieved. Diafiltration under these circumstances will also remove other small molecular weight materials such as other toxins (e.g., PCB), hormones, insecticides, and the like. The levels of endotoxin can readily be followed using commercially available methodology. Most preferred is the Limulus amoebocyte lysate assay.

When it is desired to prepare a serum which contains low levels of gamma-globulins, so as to bring these into closer coincidence with the normal ranges of fetal bovine serum, these globulins can be readily separated from the serum by standard salt precipitation steps. These salt precipitation steps are well known in the art and are, for example, described in Michl, U.S. Pat. No. 3,128,228 or Bozicevich, U.S. Pat. No. 3,429,867. Any salt capable of precipitating globulins can be used in the invention, such as ammonium sulfate, potassium sulfate, sodium sulfate, and preferably the latter. The precipitation is carried out at 25° C., by slowly adding the salt to a stirred solution of the serum, up to the prescribed levels of salts. In order to decrease globulin levels, it is preferred to add ammonium sulfate to 20%–35% of saturation, or sodium sulfate to a range of 9–16% weight per volume, preferably 12%, to serum whose pH has been adjusted to a range of 7–8. After the salt is fully dissolved, the solution is allowed to stand for 24–48 hours and the precipitated protein is separated by filtration or centrifugation. After salt addition and protein precipitation, it is necessary to remove salt which remains dissolved in the supernatant. This is normally done by dialysis, diafiltration, gel filtration, or any other such known method.

When salt fractionation of protein is included in the process, the salt separation from the supernatant by any of these methods also serves as the step of removing endotoxin, as well as insecticides, hormones and the like. Thus, under such a mode of operation it is possible to combine endotoxin removal and salt removal into one step.

An additional refining step for the serum is treatment thereof with charcoal in order to remove steroids, hormones as well as other toxic products. The term charcoal includes wood-derived or lignite-derived activated carbon. In this step, it is important to work with serum which has normal salt concentration. Thus, if a salt fractionation step has been included in the process, it is necessary, prior to charcoal treatment, to remove the salt, as by dialysis or diafiltration. Charcoal treatment of the serum can be batchwise or by immobilizing the charcoal on filter mats or pads. When batchwise, charcoal is added to a well stirred sample of serum to a range of from 20 to 200 g/l, preferably at 50–100 g/l, most preferably at 70 g/l. The charcoal-containing serum can be stirred for a period of from 1 hour to 48 hours from 0° C. to room temperature. The pH has to be adjusted to the range of from 5 to 10.5. After settling, the charcoal is separated, e.g. by centrifugation or filtration, making sure that a clear supernatant serum is obtained in the filtrate.

When the charcoal is immobilized in mats or pads, these may be loaded on a cylindric column and the serum simply flowed therethrough at an appropriate rate. This allows for a continuous process. Charcoal-containing mats, prepared by physically entrapping powdered charcoal in filter pads can be used. The use of charcoal pads, using about 1 pad per liter (70–200 g charcoal/pad) with a repeat cycle of the serum therethrough is preferred to the batch method.

The most highly refined unspiked serum of the invention is that wherein starting serum has been delipidized, salt fractionated, diafiltered or dialyzed, charcoal treated and heat inactivated. These steps can be carried out in any desired order, with the proviso that salt fractionation always be followed by removal of salt ions from supernatant.

The heat inactivation at 50°–60° C. for about 20–40 minutes, lowers the toxicity of the serum. This occurs because many toxic serum components, such as complement proteins are inactivated at relatively low temperatures.

As one final measure, the protein content of the sera of the invention can be adjusted by appropriate concentration or dilution so as to adjust the same to the desired controlled range of 3–7g/dl, preferably about 5 g/dl. At the same time electrolyte levels ($K^+$, $Na^+$, etc) can be adjusted to any desired level. Preferably they are set at $[Na^+]$=100–200 meq/liter; $[K^{30}]$=1–20 meq/liter; $[Ca^{+2}]$=1–5 meq/liter. Most preferably the values are $[Na^+]$=150 meq/liter; $[K^+]$=5–6 meq/liter; $[Ca^{+2}]$=3–4 meq/liter. The pH is adjusted to 6–8, preferably about 7.5.

Another final measure is the sterilization of the sera, as by or sterile filtration. This removes any bacteria present as contaminants. Bacterial levels are then undectable by the assay of U.S. Pharmacopeia Standards, volume 21.

Under these conditions, the sera of the invention is stable indefinitely frozen or lyophilized.

Individual sera prepared at different selected stages of the process are, of course, useful as intermediates in preparing the best, highly refined serum.

The sera of the present invention when complemented with fetal calf serum are useful in all applications wherein fetal bovine serum has been or is used. It can also be used as replacement for other growth media of the art, such as those indicated in Ham, R. G. and McKeeam W. L., supra, herein incorporated by reference. Normally, the amount of spiked serum in the tissue culture medium is in the range 2–20% by volume, most preferably about 10%. The applications include monolayer cultures, suspended cultures, and clonal cultures. The most important application is that of nutrient source for the tissue culture of animal cells in vitro. Numerous different cell lines may be grown in the present spiked culture media and the method of growing cells is not restricted to any particular cell line. For example, normal or transformed cells, and virus producing cells can be grown with the sera. Particular examples of cell lines include Chinese hamster ovary, mouse, 3T3, chicken embryo fibroblasts, duck embryo fibroblasts, human foreskin, monkey kidney, Syrian hamster kidney, baboon kidney, mouse fibroblasts, BHK, BGM, RD, DET 550, W138, HeLa, mouse lymphocytes, P815 macrocytomas, DS19 erythroleukemia, and the like. The cell lines can be grouped into two broad categories. First are the cell lines which can be grown indefinitely. They usually are transformed or tumor cells. Second are the cells which cannot be grown forever. These cells more closely resemble normal tissue.

One unique aspect of the spiked serum of the invention is that certain cell types are maintained easier therein than in FCS, due to lower metabolism and growth rate. This is particularly advantageous, for example, in viral diagnostics, where long term maintenance of cells is desirable. Controlled levels of steroids, such as estrogen, render the spiked sera of the invention particularly useful for the growth of estrogen dependent mastoma cells, which show widely variable growth rates in natural serum products.

The sera of the invention can be used by themselves ("unspiked" sera) to stimulate lymphocytes by mitogens (see Examples 24–29, below) or, in combination with natural fetal bovine serum, natural newborn calf serum or any other tissue culture medium or growth factor of the prior art as a serum for growth of cells. Particularly preferred are those combinations of the sera of the invention with natural fetal calf serum ("spiked" sera). In such mixtures, the sera of the invention may be present from 1 to 99% and fetal calf serum may be present from 99 to 1% of the mixture volume. Preferred are those mixtures wherein the amount of FCS is such that the functional growth properties of the resulting mixture approximates those of fetal calf serum, depending on the particular cell line system for which it is intended. Most preferred are those mixtures wherein the serum of the invention is present in 50–98%, and FCS is present in 2–50% by volume of the total mixture, particularly those wherein FCS is present at 5–10% by volume. Use of such mixtures is advantageous in that it decreases cost and extends the range of usefulness of the serum of the invention. The sera of the present invention can also be combined with synthetic media and synthetic growth factors.

The growth of lymphocytes or leukocyte-type cells (T cells, mitogen assays, hybridomas, etc.) is done with unspiked serum, while other cell culture work, such as that used for virus production or general cell growth, is done with spiked serum.

When growing cells in vitro, these must be periodically washed free of metabolic waste. If all necessary conditions are met, continuous or transformed cells are capable of living, growing and dividing at a constant rate year after year, and may be alive and fully vigorous many years after the animal or plant from which the tissue cells were taken would have normally died. (See for example, Giese, "Cell Physiology" 3rd. Ed., 1968, 600–601).

Having now generally described this invention, a better understanding can be obtained by reference to certain specific examples which are incorporated herein for purposes of illustration only and are not intended to be limiting of the scope of the invention or the spirit thereof.

EXAMPLE 1

Preparation of a Highly Refined Serum According to the Present Invention

1. Bovine blood was collected at slaughter from feedlot calves at about one year of age.
2. The blood was centrifuged in 1 liter polycarbonate bottles at 4200 RPM X 45 min. in a Beckman J6 centrifuge.
3. The supernatant was aspirated, pooled and run through a continuous flow centrifuge at 8000 RPM.
4. The supernatant was stir-mixed, and 30 g/liter fumed silica (AEROSIL ®) was added, mixed for 2 hours and allowed to settle overnight at 4° C.
5. The supernatant was drained off and dry sodium sulfate added at 12% w/v (120 g/liter). The mixture was stirred for 4 hours and allowed to settle overnight at 25° C.
6. The mixture was spun at 8000 RPM in a continuous flow centrifuge and filtered through a microporous filter membrane.
7. The clarified material was diafiltrated using an Amicon DC-30 diafiltration device. Four volumes of water were followed by 8 volumes of dialysis fluid.
8. After diafiltration the protein level was adjusted to about 4.0 g/100 ml and the serum was run through a column composed of charcoal impregnated filter pads. After 2 cycles the serum was collected and the protein adjusted to 5.0 g/100 ml.
9. Serum was sterile-filtered through a 0.2 m microporous (Zetapore ®) filter and bottled.
10. Serum was heat inactivated at 56° C. for 30 minutes and then stored frozen.

The biochemical characterization of the serum from Example 1 is presented in Table 2. This table also incorporates a biochemical analysis of the "Agamma" serum prepared according to Bozicevich, U.S. Pat. No. 3,429,867.

TABLE 2

| TEST PROFILE | Units | Serum of Invention | Donor Calf | Newborn Calf[1] | Fetal Calf | Agamma |
|---|---|---|---|---|---|---|

TABLE 2-continued

|  | Units | Serum of Invention | Donor Calf | Newborn Calf[1] | Fetal Calf | Agamma |
|---|---|---|---|---|---|---|
| Glucose mg/dl | mg/dl | 0 | 26 | 64 (71) | 140 | 7 |
| Bun mg/dl | mg/dl | 0.1 | 5 | 3 (13) | 14 | 0 |
| Creatinine | mg/dl | 0.3 | 1.0 | 1.1 (1.2) | 3.2 | 0.1 |
| Bun/Creat. Ratio |  | 3 | 5 | 3 (11) | 4 | 0 |
| Uric Acid | mg/dl | 0.0 | .2 | .7 (0.9) | 2.4 | 0.0 |
| Sodium | meq/l | 150 | 141 | 139 (140) | 136 | 7 |
| Potassium | meq/l | 5.7 | 5.0 | 7.0 (6.3) | 28 | 0.6 |
| Chloride | meq/l | 82 | 102 | 99 (102) | 99 | 0 |
| Carbon Dioxide | meq/l | 2 | 22 | 31 (21) | 7 | 0 |
| Calcium | mg/dl | 12.6 | 9.5 | 9.7 (7.9) | 13.5 | 4.4 |
| Ion-Ca (Approx) | meq/dl | 3.1 | 2.1 | 2.5 (1.9) | 4 | 1.3 |
| Phosphorus | mg/dl | 0.2 | 6.4 | 6.7 (5.3) | 10 | 0.1 |
| Cholesterol | mg/dl | 1 | 83 | 54 (65) | 26 | 21 |
| Triglycerides | mg/dl | 2 | 34 | 21 (24) | 23 | 7 |
| Total Protein | gm/dl | 4.4 | 6.9 | 5.3 (6.1) | 3.9 | 3.7 |
| Albumin | gm/dl | 2.81 | 3.0 | 2.8 (2.9) | 2.4 | 2.9 |
| Globulins | gm/dl | 1.58 | 3.9 | 2.5 (3.2) | 1.5 | 0.8 |
| A/G Ratio |  | 1.5 | 0.8 | 1.1 (0.9) | 1.6 | 3.6 |
| Total Bilirubin | mg/dl | 0.2 | 0 | 0.0 (0.4) | 0 | 0.0 |
| Alk Phos | mu/ml | 181 | 97 | 209 (178) | 231 | 1 |
| GGT | mu/ml | 19 | 30 | 292 (256) | 16 | 5 |
| SGOT | mu/ml | 47 |  | 1 | 16 (34) | 4719 |
| LDH | mu/ml | 870 | 690 | 153 (890) | 436 | 262 |
| Iron | mcg/dl | 267 | 169 | 107 (119) | 239 | 62 |
| PROTEIN ELECTROPHORESIS BLOOD |  |  |  |  |  |  |
| Total Protein | g/dl | 4.40 | 6.1 | 4.6 (5.1) | 3.6 |  |
| Albumin | g/dl | 2.81 | 2.52 | 2.24 (2.24) | 2.2 |  |
| Alpha 1 | g/dl | 0.49 | 1.31 | 1.106 (1.09) | 0.9 |  |
| This sample appears to have the Alpha Globulins in a single band. |  |  |  |  |  |  |
| Beta | g/dl | 0.47 | 0.65 | 0.71 (0.83) | 0.4 |  |
| Gamma | g/dl | 0.62 | 1.62 | 0.59 (0.94) | — |  |
| TOTAL LIPIDS | mg/dl | 3 | 415 | 315 | 280 | 78 |

[1]The numbers in parenthesis represent the determination for a Newborn Calf from a different commercial source.

EXAMPLE 2

I. Preparation of Cellulose Based Media Containing Fumed Silica Particulate

Large cellulosic fibers (+400 to +800 CSF) were dispersed to a 1% solids content in a water slurry. After complete dispersion, short fibrilated cellulosic fiber (+40 to −10 CSF) was added to the slurry to a 3.5% consistency. This was followed by addition of the fumed silica (Aerosil 380 ®, 7 millimicrons), anionic polymer, silicas of relatively larger sizes (such as Sipernet 22 ®) and cationic polymer.

Sufficient agitation and mixing was allowed at every stage of addition. The mixture was pumped through a 100 mesh screen vacuum forming pot, and the filter pad was formed upon the application of vacuum to decant the water. The time required for the disappearance of water inside the pot after the application of vacuum is defined as the felting time. The smaller the particle sizes in the slurry, the longer the felting time to form the filter pad. Two filters were prepared as indicated at Table 3:

TABLE 3

|  | #1 | #2 |
|---|---|---|
| Large cellulosic Coho Fiber | 20% | 20% |
| Short microflake | 10% | 10% |
| Aerosil 380 ® | 35% | 35% |
| Sipernet 22 ® | 35% | 35% |
| Polycup 1884 ® resin | 1.0% | 1.0% |
| Polystyrenesulfonate | 1.0% | — |
| Polyacrylic Acid | — | 2.0% |

Delipidization of Serum Using the Media Prepared in I

Unfiltered human serum having a lipid content of 500 mg/dl was continuously filtered through a plurality of filters 1 and a plurality of filters 2, and the reduction in lipid concentration is shown in Table 4, with reduction expressed as % lipid removal.

TABLE 4

| Serum Sample | Filter | No. of filters | Filter Weight (g) | Flow Rate (ml/min) | Δ P (psi) | Vol. filtered (ml) | % effective Removal |
|---|---|---|---|---|---|---|---|
| 1 | 10 | 15 | 7.2 | 1.6 | 10 | 30 | 37 |
|  |  |  |  |  |  | 5 | 5 |
|  |  |  |  |  |  | 5 |  |
|  |  |  |  |  |  | 20 | 70 |
|  |  |  |  |  |  | 30 |  |
|  |  |  |  |  |  | 25 | 100 |
|  |  |  |  |  |  | 40 |  |
| 2 | 18 | 8 | 6.2 | 0.6 | 20 | 20 | 30 |
|  |  |  |  |  |  | 26 | 50 |
|  |  |  |  |  |  | 45 |  |
|  |  |  |  |  |  | 30 | 5 |
|  |  |  |  |  |  | 29 |  |

The resultsd indicate that large volumes of serum can quickly and efficiently be delipidized using immobilized fumed silica.

EXAMPLE 3

Growth Experiments

Four mammalian and two avian cell lines were cultured in parallel (a) in Dulbecco's modified Eagles medium (Gibco) Supplemented with Fetal Calf Serum (FCS) (commercial) and (b) in the highly refined serum of Example 1. The efficiency with which the serum of Example 1 supports the propagation of chicken embryo fibroblasts was also compared to that of fetal calf serum. Doubling times, saturation density and passage number were compared in all cases. The results are shown in Table 5.

TABLE 5

| Cell line | Fetal serum (1) | Serum of Example 1 |
|---|---|---|
| 3T3 Mouse embryo | | |
| subculture number | >100 | 5 |
| saturation density (number cells/CM$^2$) | 2 × 10$^5$ | 2 × 10$^5$ |
| doubling time (hrs.) | 26 | 26 |
| BHK$_{21}$ Syrian hamster Kidney | | |
| subculture number | >100 | |
| saturation density | 6 × 10$^5$ | 5.5 × 10$^5$ |
| doubling time | 14 | 15 |
| BGM Buffalo green monkey Kidney | | |
| subculture number | >100 | 5 |
| saturation density | 4 × 10$^5$ | 4 × 10$^5$ |
| doubling time | 17 | 17 |
| R.D. Rhabdomyosarcoma, embryonic human | | |
| subculture number | >100 | 5 |
| saturation density | 5 × 10$^5$ | 4 × 10$^5$ |
| doubling time | 18 | 18 |
| RECC-UT 330 REV-T transformed lymphoblasts (chicken) suspension culture | | |
| subculture number | >100 | 8 |
| saturation density | 3.3 × 10$^6$ | 3.2 × 10$^6$ |
| doubling time | 15 | 17 |
| RECC-UT-1 REV-T transformed lymphoblasts (chicken) suspension culture | | |
| subculture number | >100 | 8 |
| saturation density | 3.8 × 10$^6$ | 3.5 × 10$^6$ |
| doubling time | 14 | 16 |
| Chicken embryo fibroblast (primary culture) | | |
| maximum subculture number | 9–10 | 6–7 |
| saturation density | 1 × 10$^5$ | 1 × 10$^5$ |
| doubling time | 24 | 27 |

(1) Dulbecco's Modified Supplemented with 10% FCS.

These results indicate the suitability of the serum of the invention to culture a variety of different cells.

EXAMPLE 4

Clonal Cell Growth/Toxicity Assay

Chinese Hamster ovary cells were plated on 75 mm plastic tissue culture plates at 300 cells/plate. After 7 days in culture, macroscopic colonies were counted. This test is generally considered one of the most stringent of the cell culture assays.

The results are shown in Table 6.

TABLE 6

| Serum | Relative Plating Efficiency |
|---|---|
| FCS, 10% | 100% |
| Serum of Example 1, 10% | 95% |
| Serum of Example 1, 9% plus FCS, 1% | 95% |
| FCS, 10% | 100% |
| FCS, 5% | 88.6% |
| Serum of Example 1, 10% | 86.5% |
| Serum of Example 1, 5% | 84.0% |

These results indicate that the refined serum of the invention is similar to FCS in its cell growth support abilities.

EXAMPLE 5

Coxsacki B3 virus was titrated in BGMK cells grown in 10% FCS vs. 10% serum of Example 1. No difference was seen in the yield of viruses after growth in either serum.

EXAMPLE 6

Growth of Hybridomas

Hybridoma P-3 carrier cells have been grown successfully in the serum of Example 1. Population doubling time, saturation density and cell morphology are essentially equal in both FCS and in the serum of Example 1.

EXAMPLE 7

Induction and assay of mouse fibroblast interferon (beta-type) and mouse immune interferon (gamma-type): Comparison of Reheis ® fetal calf and invention serum.

A. Methods 1. Induction of Interferon in Mouse Fibroblasts

L-929 cells, a continuous line of murine fibroblasts, were adapted for growth in either Reheis ® fetal calf serum or invention (Example 1) serum by growing the cells in RPMI 1640 medium supplemented with these sera for 6 passages (approximate 60 cell doublings). Mouse fibroblast interferon was induced in these adapted cells with polyinosinic: polycytidylic acid (poly I:C), a synthetic double-stranded polynucleotide polymer which is a potent interferon inducer, by methods described in the art (Straub, Garry and McGee, 1974, Infection and Immunity 10:783–792; Garry and Waite, 1979, Virology 96:120–128). Briefly 100 μg/ml of poly 1:C was added to cultures of L-929 fibroblast which had been adapted to either Reheis ® or Example 1 serum. After 1 hour for adsorption of the polymer, the cells were washed extensively and medium was replaced in the culture. Interferon was harvested from the cells at eight hours, which is the optimum time for interferon production. Mouse fibroblast interferon was treated at pH 2 for 2 days at 4° C.

2. Induction of Mouse Immune Interferon (Gamma-Type Interferon)

Mouse immune interferon was induced in mouse spleen cells by published techniques. Briefly mouse spleen cells were obtained from mice sacrificed by cervical dislocation. Lymphocytes were separated from erythrocytes by density centrifugation over Ficol-hypaque. Immune type mouse interferon was induced with 1 μg/ml phytohemagglutinin-O (Sigma). Interferon was harvested 4 hrs. after induction.

3. The Plaque Reduction Assay for Murine Interferons on Mouse Cells Adapted to Reheis ® or Example 1 Serum Mouse fibroblast and immune interferons were assayed by a standard virus plaque reduction assay. Briefly, dilution (Log$_2$) of interferon samples were added to confluent monolayers of L-929 cells adapted to both Reheis ® or Example 1 serum. After 1 hour for binding of the interferon, medium was added to the cultures and incubated for an additional 8 hours to establish the interferon-induced antiviral state. At this time the cultures were challenged with Vesicular Stomatitis Virus (vsv—Indiana strain) then overlayed with RPMI 1640 medium supplemented with 0.9% Bacto agar and either Reheis ® or Example 1 sera. Plaques were visualized 48 hrs. later by counterstaining with neutral red dye. One unit of interferon is defined as the amount of interferon needed to reduce the number of VSV plaques by 50%.

B. Results

The results of the comparison of mouse cells adapted to Reheis ® or Example 1 serum to induce and assay interferons are summarized in Table 7.

TABLE 7

| Type of Interferon | Source | Interferon Titer Assay on L-929 cells grown in Reheis ® serum | Assayed on L-292 cells grown in Example 1 serum |
|---|---|---|---|
| fibroblast interferon | L-929 cells grown in Reheis ® | 528 units/ml | 462 units/ml |
| | L-929 cells grown in Example 1 serum | 660 units/ml | 660 units/ml |
| immune interferon | mouse splenocytes | 297 units/ml | 330 units/ml |

C. Conclusions

The serum of the invention is equal to Reheis ® fetal calf serum in supporting induction of mouse fibroblast interferon. The serum of the invention is equal to Reheis ® fetal calf serum in the assay of mouse fibroblast or immune type interferon.

EXAMPLE 8

Comparison of the Growth Kinetics of VSV in Mouse Cells Adapted to Reheis ® Fetal Calf Serum or Serum of the Invention A. Methods 1. Cultures of L-929 cells adapted to RPMI medium supplemented with either Reheis ® fetal calf serum or serum of Example 1 were infected with VSV at a multiplicity of infection of 0.01 plaque forming units/cell. After 1 hour for virus adsorption the cells were washed extensively and the cultures replaced with RPMI supplemented with Reheis ® or serum of Example 1. Virus was sampled at hourly intervals and the medium replaced with fresh medium. Virus was titrated on L-292 cells as described supra (Garry and Waite, 1979). Briefly, the samples containing virus were diluted ($Log_{10}$). Samples of the dilution were added to monolayers of L-929 cells. After 1 hour for virus adsorption the cultures were overlayed with RPMI medium supplemented with calf serum and 0.9% Bacto agar.

B. Results

1. The growth kinetics of VSV in L-292 cells cultured in medium containing Reheis ® fetal calf serum or Example 1 serum are presented in FIG. 1.

C. Conclusions

The growth kinetics of VSV in L-929 cells grown in medium supplemented with Reheis ® fetal bovine serum or serum of the invention are indistinguishable.

EXAMPLE 9

Comparison of Serum of the Invention with Calf Serum (Kansas Biological) in Mitogen Assay Two four month old mice were killed by cervical dislocation. The spleens were removed and mashed through small mesh screens with rubber-tiped syringes, into RPMI (1% pen-strep, 0.5% Fungizone) with either 5% calf serum (CS-KC Biologicals), or 5% Example 1 serum. The cells were washed at 1200 rpm for 10 min. They were diluted, counted and dispersed in 1 ml aliquots into 12×75 mm tubes. Two different cell quantities were tested ($10^6$ and $4 \times 10^6$). Phytohemogglutinin-A (PHA) was added to quadruplicate cultures. Duplicate cultures served as controls. Three different PHA concentrations were tested (1, 2.5, and 5 µl/ml. The cultures were then incubated for 48 hours, at which time 0.1 ml (2 µCi) tritiated thymidine was added to each tube. After a 23 hour pulse, the cells were vortexed and poured onto glassfiber filters. The tubes were washed twice with media. The filters were washed twice with 6% trichloroacetic acid (TCA) and twice with ethanol, placed in scintillation vials with Bray's solution, and counted in the scintillation counter. The results are shown in Table 8.

TABLE 8

| | +PHA | −PHA |
|---|---|---|
| (1) $10^6$ cells, 5 µl/ml PHA | | |
| CS (Kansas Biol) | 869 ± 647 | 833 ± 321 |
| Serum of Example 1 | 3,548 ± 616 | 3,218 ± 296 |
| (2) $4 \times 10^6$ cells, 5 µl/ml PHA | | |
| CS | 50,398 ± 14,120 | 6,427 ± 1,114 |
| Serum of Example 1 | 42,097 ± 5,218 | 20,825 ± 711 |
| (3) $10^6$ cells, 2.5 µl/ml PHA | | |
| CS | 1,549 ± 970 | 989 ± 32 |
| Serum of Example 1 | 15,062 ± 3,124 | 2,574 ± 428 |
| (4) $4 \times 10^6$ cells, 2.5 µl.ml PHA | | |
| CS | 56,339 ± 3,243 | 7,492 ± 760 |
| Serum of Example 1 | 61,311 ± 19,734 | 18,120 ± 3,118 |
| (5) $10^6$ cells, µl/ml PHA | | |
| CS | 893 ± 432 | 983 ± 206 |
| Serum of Example 1 | 1,930 ± 4,712 | 2,746 ± 755 |
| (6) $4 \times 10^6$ cells, 1 µl/ml PHA | | |
| CS | 20,419 ± 9,026 | 6,464 ± 35 |
| Serum of Example 1 | 39,233 ± 14,372 | 21,581 ± 683 |

Conclusion

The serum of the invention substantially enhances the ability of mouse splenic lymphoctes to respond to PHA relative to quality calf serum.

EXAMPLE 10

In vitro Transformation of Immature Lymphocytes by Reticuloendotheliosis Virus (REV-T)

TABLE 9

|  | Example 1 Serum | FCS |
|---|---|---|
|  | x ± s.d. |  |
| Control | 514 ± 11 colonies/plate | 212 ± 62 colonies/plate |
| 1 × viral stock | 496 ± 136 colonies/plate | 353 ± 19 colonies/plate |
| 1/15 × viral stock | 547 ± 24 colonies/plate | 367 ± 73 colonies/plate |

Due to the appearance of large numbers of macroscopic colonies on the nonvirus-treated control plates, plates were examined microscopically to determine the percentage of true transformed colonies. In Table 10, the data have been corrected to reflect the number of true transformants.

TABLE 10

|  | Example 1 Serum | FCS |
|---|---|---|
| Control | 0 | 0 |
| 1 × viral stock | 40 colonies/plate | 53 colonies/plates |
| 1/15 × viral stock | 27 colonies/plate | 48 colonies/plates | corrected for # true transformants/$10^7$ spleen cells
= number of macroscopic colonies x % colonies that are true transformants for each dilution While both sets of control plates appear to contain large numbers of macroscopic colonies, the colonies appearing on Reheis ® control plates were clumps of nonproliferating cells which could be easily distinguished macroscopically from REV-T transformed clones. In contrast, macroscopic colonies appearing on invention control plates were composed of proliferating cells that resembled macrophase/granulocyte CFU's. These colonies were large and difficult to distinguish macroscopically from true REV-Transformed clones. Furthermore, it is possible that these macrophage/granulocyte-like colonies inhibited the proliferation of REV-transformed clones. Therefore, this colony-stimulating activity may make the sera of the invention unsuitable for in vitro transformation assay employing cells of the hematopoietic origin.

Conclusions

The serum of the invention appears to promote the growth of normal macrophages far more efficiently than Reheis ® serum. Calf serum frequently contains inhibitors of macrophage growth (lipoproteins) which have been removed from the serum of the invention. The overgrowth of these macrophages, however, makes assaying hematopoietic cell transformation more difficult. Microscope colony examination is required to distinguish transformants from normal colonies. Serum of the invention could be used to facilitate the establishment of macrophage cultures.

EXAMPLES 11-22

Ability of Invention Serum, Reheis ® Fetal Calf and Kansas Biological Calf Serum to Support Cell Growth

Introduction

In order to test the growth and maintenance potential of the serum of the invention, the following cell lines were subcultured:
3T—Embryo, mouse
BHK—Kidney, Syrian or Golden hamster
BGM—Buffalo Green Monkey Kidney
RD—Rhabdo myosarcoma, embryonal, Human
DET 550—skin, Human
W138—lung, diploid, Human
HeLA—Epithelial carcinoma, cervix, Human Chick embryo fibroblasts (CEF) were also subcultured and maintained. In addition, CEF's and avian hematopoetic cells transformed by reticuloendotheliosis virus were tested.

The growth and maintenance parameters examined were passage number, generation time, saturation density, and cell viability.

All of the cell lines were subcultured approximately twice a week for twenty-five weeks using Dulbecco's Modified Eagle's medium (DME) supplemented with 10% serum.

EXAMPLE 11

Chick Embryo Fibroblasts (CEF); Media: Dulbecco's Modified Eagle (DME) (Flow lab)
Test (1) Primary CEF's were prepared according to the procedure of Bose & Levine (J. Virol. 6:1117–1121) from 10 day SPAFAS embryos. Primary CEF's were routinely subcultured three days after the first plating and then every other day thereafter. Upon each passage the cells were split one flask into two (1:2 split).

(2) CEF's were also monitered to assay the maintenance potential of the invention (Example 1) sera. CEF secondary cells were fed every two days using DME supplemented with 5% serum. This schedule was kept until cell death. Microscopic examination and trypan blue exclusion were used as parameters of viabilith.

(3) CEF secondary cells infected with reticuloendotheliosis virus (REV-T) were subcultured every two days using DME supplemented with 10% serum.

TABLE 11

| Propagation of CEF | | | | |
|---|---|---|---|---|
|  |  |  | Invention | |
| t-0 | FCS | CS | Lot I | Lot II |
| (b) # cells/cm² | 2.9 × 10⁴ | 2.9 × 10⁴ | 2.9 × 10⁴ | 2.9 × 10⁴ |
| 18 hr | 3.75 × 10⁴ | 2.6 × 10⁴ | 3.3 × 10⁴ | 2.9 × 10⁴ |
| 40 hr | 6.25 × 10⁴ | 4.7 × 10⁴ | 5.5 × 10⁴ | 4.8 × 10⁴ |
| 48 hr | 7.3 × 10⁴ | 5.7 × 10⁴ | 6.8 × 10⁴ | 5.7 × 10⁴ |
| 72 hr | 1 × 10⁵ | 9 × 10⁴ | 9 × 10⁴ | 9 × 10⁴ |
| Fresh media added but cells not subcultured | | | | |
| 120 hr | 1.82 × 10⁵ | 1.14 × 10⁵ | 1.33 × 10⁵ | 1.25 × 10⁵ |
| Subculture number (max) | 12 | 5 | 7 | 9 |
| Saturation density (cells/cm²) | 1.8 × 10⁵ | 1.1 × 10⁵ | 1.35 × 10⁵ | 1.25 × 10⁵ |
| Doubling time (hrs) ave | 40 | 48 | 40 | 42 |

TABLE 12

Propagation of REV-T transformed fibroblasts

|  | FCS | CS | Invention Lot #1 | Invention Lot #2 |
|---|---|---|---|---|
| t-0 | $3 \times 10^4$ | $3 \times 10^4$ | $3 \times 10^4$ | $3 \times 10^4$ |
| t-18 Infection is/REV-T | $2.8 \times 10^4$ | $2.1 \times 10^4$ | $2.3 \times 10^4$ | $2.5 \times 10^4$ |
| t-2 24 | $3.5 \times 10^4$ | $2.5 \times 10^4$ | $2.7 \times 10^4$ | $3.0 \times 10^4$ |
| t3 48 | $6 \times 10^4$ | $3.4 \times 10^4$ | $4 \times 10^4$ | $4.5 \times 10^4$ |
| 72 Δ media | $1.2 \times 10^5$ | $5 \times 10^4$ | $6 \times 10^4$ | $7 \times 10^4$ |
| 96 | $2.5 \times 10^5$ | $3 \times 10^4$ | $85 \times 10^4$ | $1 \times 10^4$ |
| 120 | $3.2 \times 10^5$ | — | $1.0 \times 10^5$ | $1.80 \times 10^5$ |
|  | — | — | $1.0 \times 10^5$ | $6 \times 10^4$ |
| 160 | — | — | — | — |
| Subculture # | 35 | 2 | 11 | 12 |
| Saturation density cells/cm² | $3.2 \times 10^5$ | $5 \times 10^4$ | $1 \times 10^4$ | $1.8 \times 10^5$ |
| Ave. doubling time | 24 | NA | 72 | 60 |

The results are shown in Tables 11, 12.

Figure 2:
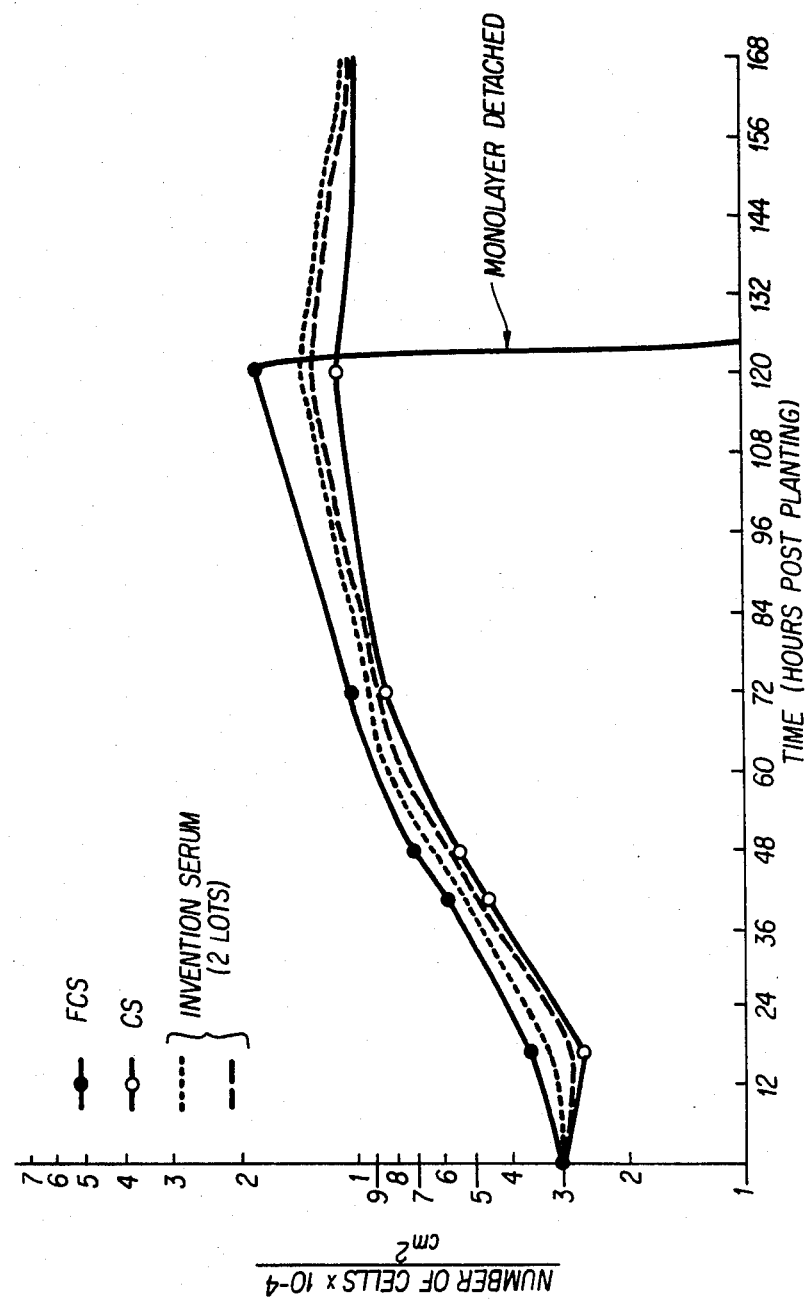
FIG. 2 compares the growth of Chicken Embryo Fibroblast (CEF) cells in FCS, in Calf Serum(CS) and in 2 lots of Zeta serum of the invention. See Example 11.

(1) CEF's passaged in invention serum remained healthy and dividing until passage 8-9. At this point, the cells appeared granulated and less than 20% attached in the next passage. Those cells which did attach rarely divided; within 30 hours, all cells were dead. Cells passaged with Reheis ® Fetal Calf serum were viable into passage 11 before declining with a similar pathology as the cells with invention Serum. CEF's subcultured only 5-6 passages in medium supplemented with calf serum (FIG. 2).

(2) CEF secondary cells could be maintained and remained as healthy (non-granulated, attached and viable) monolayers for 12-14 days before monolayer detachment. Cells maintained in Reheis ® fetal bovine sera remained healthy for 4-5 days prior to dettachment. Cells maintained in calf serum survived 14-15 days.

(3) CEF secondary cells infected with REV-T became transformed (altered cell morphology visible at 5 days, generation time, saturation density) and could be passaged through twelve subcultures with the invention sera.

Calf serum supports transformation of CEF secondary cultures with REV-t, but does not meet the growth requirements of the transformed cells beyond two passages.

Figure 3:
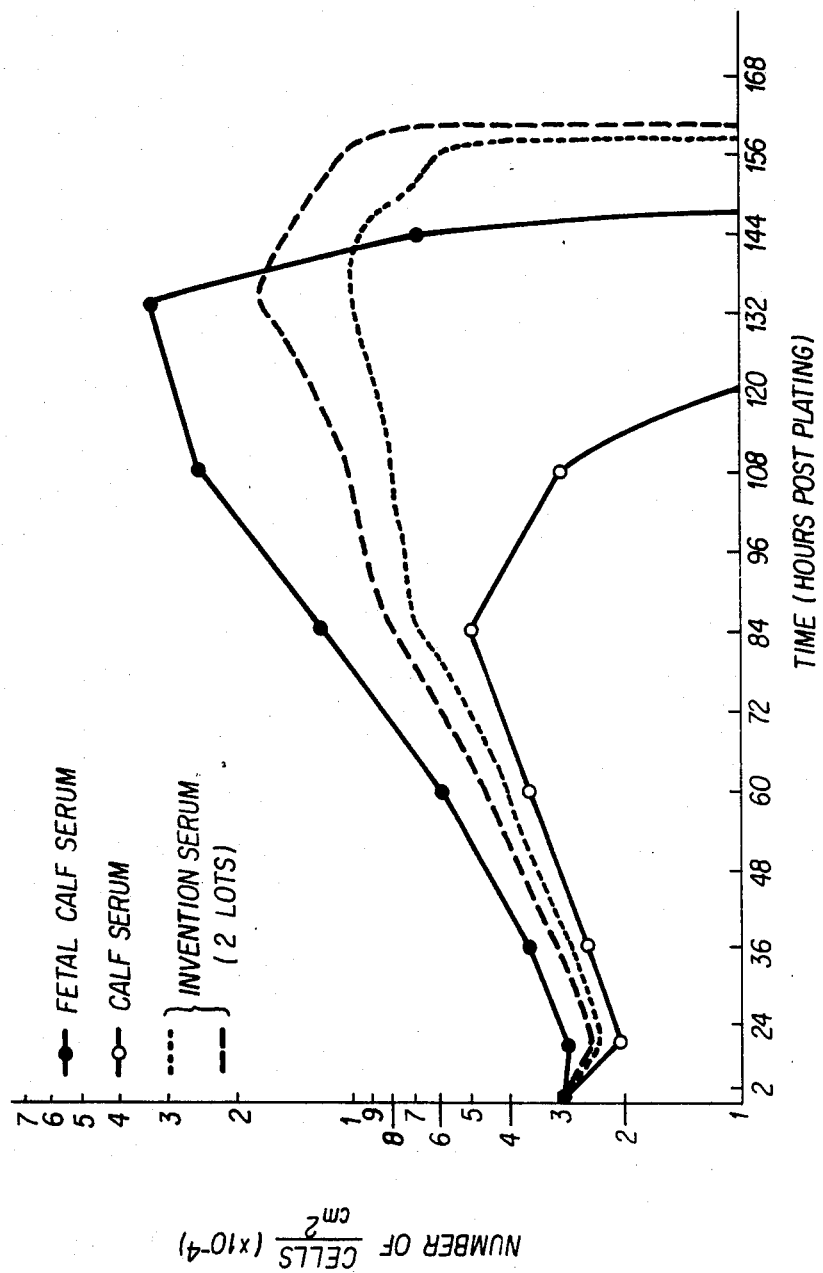
FIG. 3 compares the growth of CEF infected with REV-T in FCS, CS and two lots of Zeta Serum. See Example 11.

Reheis ® Fetal calf serum supports transformation and supports cell growth and division for up to 35 passages (FIG. 3).

Conclusion

Invention sera performed much better than calf serum in its ability to promote CEF cell growth and division, and is comparable in its ability to maintain healthy monolayers. In comparison to fetal calf serum, invention sera performed slightly poorer in the promotion of cell growth and division but did maintain healthy monolayers twice as long. FCS stimulated the CEF's into division past the point of confluency resulting in stress and dettachment of the monolayer.

Transformed fibroblasts have a much increased growth requirement. Calf serum cannot maintain the growth and division of these cells. The invention sera did support the REV-T transformed fibroblasts through 12 subcultures and a generation time of approximately 40 hours. Fetal calf serum supports these cells through 35 subcultes with a generation time of approximately 24 hours.

EXAMPLE 12

REV-T Transformed Hematopoietic Cells

Two clones of REV-T (reticuloendotheliosis virus) transformed avian spleen cells were cultivated in DME supplemented with invention sera. Fetal calf serum were used also as comparative controls. Cloning efficiency was also tested.

Results

Both clones KBMC and C4#1 grew well in the DMC with invention sera. Both clones underwent greater than one hundred doublings in this sera and showed no signs of ill health.

|  |  | Invention Sera | |
|---|---|---|---|
| RPMI + FCS | RPMI + CS | RPMI + Lot I | RPMI + Lot II |
| Cloning efficiency | | | |
| >75% | 20% | 50% | 70% |

Conclusions

Invention serum supports the growth of REV-T transformed spleen cells with a very slight reduction in doubling time, saturation density, and cloning efficiency.

EXAMPLE 13

KBMC REV-T transformed chicken bone marrow cells were grown—Results are shown in Table 13. Culture media: RPMI 1640 supplemented with 10% Fetal Calf (FCS) Calf (CS) or Invention Serum.

TABLE 13

|  | FCS | CS | Invention Lot I | Lot II |
|---|---|---|---|---|
| t-0 KBMC cells/ml | $2.0 \times 10^5$ | $2.0 \times 10^5$ | $2.0 \times 10^5$ | $2.0 \times 10^5$ |
| 12 hrs | $3.2 \times 10^5$ | $2.5 \times 10^5$ | $3.0 \times 10^5$ | $3.0 \times 10^5$ |
| 24 hrs | $6 \times 10^5$ | $5 \times 10^5$ | $5.5 \times 10^5$ | $5.7 \times 10^5$ |
| 36 hrs | $1 \times 10^6$ | $8 \times 10^5$ | $1 \times 10^5$ | $1 \times 10^6$ |
| 48 hrs | $1.1 \times 10^6$ | $1.4 \times 10^6$ | $1.6 \times 10^6$ | $1.6 \times 10^6$ |
| 60 hrs Δ media | $3.2 \times 10^6$ | $2.0 \times 10^6$ | $3.1 \times 10^6$ | $3.2 \times 10^6$ |
| 72 hrs | $3.8 \times 10^6$ | $3.2 \times 10^6$ | $3.5 \times 10^6$ | $3.6 \times 10^6$ |
| Subculture # | >100 | >100 | >100 | >100 |
| Saturation density max cells/ml | $3.8 \times 10^6$ | $3.2 \times 10^6$ | $3.5 \times 10^6$ | $3.5 \times 10^6$ |
| Average doubling time (hrs) | 15 | 8 | 6 | 6 |

EXAMPLE 14

C4#1 REV-T transformed chicken spleen cells (non-virus producing) were grown in culture media = RPMI + 10% sera, as indicated in Table 14:

TABLE 14

|  | FCS | CS | Invention Lot I | Lot II |
|---|---|---|---|---|
| t-0 | $2 \times 10^5$ | $2 \times 10^5$ | $2 \times 10^5$ | $2 \times 10^5$ |
| 12 hrs | $3 \times 10^5$ | $2.3 \times 10^5$ | $2.4 \times 10^5$ | $2.5 \times 10^5$ |
| 24 hrs | $5.4 \times 10^5$ | $4.1 \times 10^5$ | $4.5 \times 10^5$ | $5 \times 10^5$ |
| 36 hrs | $8.8 \times 10^5$ | $6 \times 10^5$ | $7 \times 10^5$ | $7.9 \times 10^5$ |
| 48 hrs | $1.8 \times 10^6$ | $1 \times 10^6$ | $1.2 \times 10^6$ | $1.5 \times 10^6$ |
| 60 hrs Δ media | $3 \times 10^6$ | $1.4 \times 10^6$ | $1.6 \times 10^6$ | $2 \times 10^6$ |
| 72 hrs | $3.2 \times 10^6$ | $2.2 \times 10^6$ | $3.0 \times 10^6$ | $3.2 \times 10^6$ |

TABLE 14-continued

|  | FCS | CS | Invention Lot I | Invention Lot II |
|---|---|---|---|---|
| 84 hjrs | $3.2 \times 10^6$ | $2.4 \times 10^6$ | $3.0 \times 10^6$ | $3.2 \times 10^6$ |
| Subculture # | >100 | >100 | >100 | >100 |
| Saturation density cells/ml | $3.2 \times 10^6$ | $2.4 \times 10^5$ | $3.0 \times 10^6$ | $3.2 \times 10^6$ |
| Average doubling time hrs | 16 | 22 | 20 | 18 |

EXAMPLES 15–21

Propagation of Mammalian Cell Lines

Invention sera (2 lots) were tested for their effectiveness in supporting growth and division of the following cell lines.

| (1) BHK-21 | (Kidney Syrian or Golden Hamster) |
|---|---|
| (2) 3T3 | (Embryo, Mouse) |
| (3) HeLa | (Epitheloid carcinoma, Cervix, Human) |
| (4) RD | (Rhadtomyosarcoma, Embryonal, Human) |
| (5) BGM | (Buffalo Green Monkey Kidney) |
| (6) Detroit 550 | (Skin, Human) |
| (7) WI38 | (Lung, Diploid, Human) |

Reheis® fetal calf serum and KC Biologicals calf serum were usd as comparisons. All of the above cell lines were subcultured one to two times weekly using Dulbecco's Modified Eagle (DME) (Flow lab) supplemented with 10% serum. All serum was heat-inactivated 56° C. for 30 min. prior to use. The pH of the media was kept at 7.1–7.2. The cells were microscopically examined daily to monitor their health and viability. The following growth parameters were measured.
(1) Average doubling time
(2) Saturation density
(3) Passage number
(4) Plating efficiency (A) Propagation of Cell Lines with Infinite Growth Potential (1) BHK-21, 3T3, HeLa, BGM, RD BHK, 3T3, BGM and RD are all continuous cell lines certified by ATCC. All have infinite life span. These lines were cultured in Dulbecco's Modified Eagle's medium (pH 7.2) supplemented with 10% bovine serum (invention, Calf serum (KB) or Fetal Calf (Reheis®)). The cells were examined daily for qualitative growth changes—granulation rounding cells, confluency. Each line was subcultured upon reaching monolayer confluency. In addition quantitative growth parameters were checked every twenty passages—doubling time, saturation density, plating efficiency.

Results

All of the above cell lines were still healthy, dividing cultures after more than fifty passages in the invention sera. No signs of granulation, doubling time lag, or decreased plating efficiency have been observed in the invention sera- or the fetal calf-supplemented cultures.

EXAMPLE 15

Propagation of BHK$_{21}$ Cells

TABLE 15

| t-0 | Passage # | FCS | CS | Invention Lot I | Invention Lot II |
|---|---|---|---|---|---|
| cells/cm$^2$ | 5 | $3.6 \times 10^4$ | $3.6 \times 10^4$ | $3.6 \times 10^4$ | $3.6 \times 10^4$ |
| added | 20 | $3.6 \times 10^4$ | $3.6 \times 10^4$ | $3.6 \times 10^4$ | $3.6 \times 10^4$ |
|  | 50 | $3.6 \times 10^4$ | $3.6 \times 10^4$ | $3.6 \times 10^4$ | $3.6 \times 10^4$ |
| 10 hr | 5 | $7.0 \times 10^4$ | $6.1 \times 10^4$ | $6.5 \times 10^4$ | $7.0 \times 10^4$ |
| cells/cm$^2$ | 20 | $7.0 \times 10^4$ | $6.0 \times 10^4$ | $6.4 \times 10^4$ | $7.0 \times 110^4$ |
|  | 50 | $6.9 \times 10^4$ | $6.0 \times 10^4$ | $6.5 \times 10^4$ | $8.3 \times 10^4$ |
| 24 hr. | 5 | $2.0 \times 10^5$ | $1.2 \times 10^5$ | $2 \times 10^5$ | $2. \times 10^5$ |
| cells/cm$^2$ | 20 | $2.0 \times 10^5$ | $1.0 \times 10^5$ | $2 \times 10^5$ | $2 \times 10^5$ |
|  | 50 | $2.1 \times 10^5$ | $1.0 \times 10^5$ | $1.9 \times 10^5$ | $2.1 \times 10^5$ |
| 34 hr | 5 | $2.7 \times 10^5$ | $2 \times 10^5$ | $2.5 \times 10^5$ | $2.8 \times 10^5$ |
| cells/cm$^2$ | 20 | $2.8 \times 10^5$ | $2 \times 10^5$ | $2.5 \times 10^5$ | $2.6 \times 10^5$ |
|  | 50 | $2.6 \times 10^5$ | $2.0 \times 10^5$ | $2.4 \times 10^5$ | $2.8 \times 10^5$ |
| 48 hr | 5 | $6.0 \times 10^5$ | $4.5 \times 10^5$ | $5.0 \times 10^5$ | $5.3 \times 10^5$ |
| cells/cm$^2$ | 20 | $6.0 \times 10^5$ | $4.6 \times 10^5$ | $5.0 \times 10^5$ | $5.2 \times 10^5$ |
|  | 50 | $6.0 \times 10^5$ | $4.8 \times 10^5$ | $5.2 \times 10^5$ | $5.5 \times 10^5$ |
| Δ media 72 hrs | 5 | $6.7 \times 10^5$ | $4.8 \times 10^5$ | $6.0 \times 10^5$ | $6.1 \times 10^5$ |
| cells/cm$^2$ | 20 | $6.5 \times 10^5$ | $5.0 \times 10^5$ | $6.0 \times 10^5$ | $6.2 \times 10^5$ |
|  | 50 | $6.5 \times 10^5$ | $5.0 \times 10^5$ | $6.0 \times 10^5$ | $6.2 \times 10^5$ |
| Subculture number (max) |  | >100 | >100 | >100 | >100 |
| Saturation Density # cell/cm$^2$ |  | $6.5 \times 10^5$ | $5 \times 10^5$ | $6 \times 10^5$ | $6.2 \times 10^5$ |
| Doubling time (hrs) AV |  | 14 | 16 | 14 | 14 |

EXAMPLE 16

Propagation of Mouse 3T3 Cells

TABLE 16

| t-0 | Passage # | FCS | CS | Invention Lot I | Invention Lot II |
|---|---|---|---|---|---|
| cells/cm$^2$ | 5 | $2.6 \times 10^3$ | $2.6 \times 10^3$ | $2.6 \times 10^3$ | $2.6 \times 10^4$ |
| (added) | 20 | $2.6 \times 10^3$ | $2.6 \times 10^3$ | $2.6 \times 10^3$ | $2.6 \times 10^4$ |
|  | 50 | $2.6 \times 10^3$ | $3.6 \times 10^3$ | $2.6 \times 10^3$ | $2.6 \times 10^4$ |
| 10 hr | 5 | $2.4 \times 10^3$ | $2.0 \times 10^3$ | $2.2 \times 10^3$ | $2.2 \times 10^4$ |
| cells/cm$^2$ | 20 | $2.2 \times 10^3$ | $2.0 \times 10^3$ | $2.1 \times 10^3$ | $2.15 \times 10^4$ |
|  | 50 | $1.9 \times 10^3$ | $1.8 \times 10^3$ | $1.8 \times 10^3$ | $1.84 \times 10^4$ |
| 34 hr | 5 | $4.6 \times 10^3$ | $4.4 \times 10^3$ | $4.6 \times 10^3$ | $4.5 \times 10^4$ |

TABLE 16-continued

| t-O | Passage # | FCS | CS | Invention Lot I | Invention Lot II |
|---|---|---|---|---|---|
| cells/cm$^2$ | 20 | $4.4 \times 10^3$ | $4.2 \times 10^3$ | $4.2 \times 10^4$ | $4.2 \times 10^4$ |
|  | 50 | $4.3 \times 10^3$ | $4 \times 10^3$ | $3.5 \times 10^3$ | $4 \times 10^4$ |
| 58 hr | 5 | $7.5 \times 10^3$ | $7.4 \times 10^3$ | $7.0 \times 10^3$ | $7.0 \times 10^4$ |
| cells/cm$^2$ | 20 | $7.3 \times 10^3$ | $7.2 \times 10^3$ | $7.1 \times 10^3$ | $7.2 \times 10^4$ |
|  | 50 | $7.0 \times 10^3$ | $6.8 \times 10^3$ | $6.9 \times 10^3$ | $6.95 \times 10^4$ |
| 82 hr | 5 | $1.3 \times 10^4$ | $9.2 \times 10^3$ | $1.0 \times 10^4$ | $1.1 \times 10^5$ |
| cells/cm | 20 | $1.1 \times 10^4$ | $9.0 \times 10^3$ | $1.0 \times 10^4$ | $1.1 \times 10^5$ |
|  | 50 | $9 \times 10^3$ | $8.6 \times 10^3$ | $9 \times 10^5$ | $9 \times 10^4$ |
| Δ media | 5 | $2.2 \times 10^4$ | $2.0 \times 10^4$ | $2.1 \times 10^4$ | $2.3 \times 10^5$ |
| 72 hours | 20 | $2.1 \times 10^4$ | $1.8 \times 10^4$ | $2.1 \times 10^4$ | $2.2 \times 10^5$ |
|  | 50 | $2.0 \times 10^4$ | $1.8 \times 10^4$ | $2.0 \times 10^4$ | $2.0 \times 10^5$ |
| 154 hr |  | $4.2 \times 10^4$ | $3.8 \times 10^4$ | $4.0 \times 10^4$ | $4.1 \times 10^4$ |
|  |  | $4.1 \times 10^4$ | $3.7 \times 10^4$ | $3.9 \times 10^4$ | $4.0 \times 10^4$ |
|  |  | $4 \times 10^4$ | $3.7 \times 10^4$ | $3.9 \times 10^4$ | $3.9 \times 10^4$ |
| Subculture number (max) |  | >100 | 50 | 50 | 50 |
| Saturation Density # cell/cm$^2$ |  | $4.1 \times 10^4$ | $3.8 \times 10$ | $3.9 \times 10$ | $4.0 \times 10$ |
| Doubling time (hrs) ave |  | 48 | 49 | 48 | 48 |
| Plat. efficiency (%) |  | 25 | >10 | 20 | 20 |

EXAMPLE 17

Propagation of HeLa Cells

TABLE 17

| t-O | FCS | CS | Invention Lot I | Invention Lot II |
|---|---|---|---|---|
| cells/cm$^2$ | $2 \times 10^4$ | $2 \times 10^4$ | $2 \times 10^4$ | $2 \times 10^4$ |
| 12 hr | $3 \times 10^4$ | $2.2 \times 10^4$ | $2.5 \times 10^4$ | $2.8 \times 10^4$ |
| 24 hr | $6 \times 10^4$ | $3.6 \times 10^4$ | $4.3 \times 10^4$ | $4.5 \times 10^4$ |
| 48 hr | $1.3 \times 10^5$ | $7 \times 10^4$ | $1 \times 10^5$ | $1.1 \times 10^5$ |
| Δ media |  |  |  |  |
| 72 hr | $3.2 \times 10^5$ | $2.0 \times 10^5$ | $2.6 \times 10^5$ | $2.8 \times 10^5$ |
| 96 hr | $7.0 \times 10^5$ | $5 \times 10^5$ | $6.4 \times 10^5$ | $6.4 \times 10^5$ |
| 120 hr | $7.1 \times 10^5$ | $5.2 \times 10^5$ | $6.6 \times 10^5$ | $6.5 \times 10^5$ |
| Subculture # | >50 | >50 | 50 | 50 |
| Saturation density cells/cm$^2$ | $7 \times 10^5$ | $5.2 \times 10^5$ | $6.6 \times 10^5$ | $6.5 \times 10^5$ |
| Doubling time ave (hrs) | 18 | 22 | 20 | 20 |
| Plating efficiency (%) | 50 | 20 | 40 | 45 |

EXAMPLE 18

Propagation of Buffalo Green Monkey Kidneys Cells

TABLE 18

|  | FCS | CS | Invention Lot I | Invention Lot II |
|---|---|---|---|---|
| t-0 | $2 \times 10^4$ | $2 \times 10^4$ | $2 \times 10^4$ | $2 \times 10^4$ |
| t-1 18 | $2.1 \times 10^4$ | $1.1 \times 10^4$ | $1.5 \times 10^4$ | $2.0 \times 10^4$ |
| t-2 48 | $8 \times 10^4$ | $5 \times 10^4$ | $8.6 \times 10^4$ | $9 \times 10^4$ |
| t-3 72 | $1.8 \times 10^5$ | $1.2 \times 10^5$ | $1.7 \times 10^5$ | $2 \times 10^5$ |
| Δ media | $3.1 \times 10^5$ | $2.0 \times 10^5$ | $2.9 \times 10^5$ | $3.5 \times 10^5$ |
| 120 | $3 \times 10^5$ | $2.0 \times 10^5$ | $2.9 \times 10^5$ | $3.2 \times 10^5$ |
| Subculture # | 50 | 50 | 50 | 50 |
| Saturation time | 18 | 20 | 18 | 18 |
| Plating efficiency | 20 | <10 | 15 | 15 |

EXAMPLE 19

TABLE 19

|  | FCS | CS | Invention Lot I | Invention Lot II |
|---|---|---|---|---|
| t-0 cells/cm$^2$ | $2 \times 10^4$ | $2 \times 10^4$ | $2 \times 10^4$ | $2 \times 10^4$ |
| 12 hrs | $2.8 \times 10^4$ | $2.1 \times 10^4$ | $2.2 \times 10^4$ | $2.5 \times 10^4$ |
| 24 hrs | $4.1 \times 10^4$ | $3 \times 10^4$ | $3.8 \times 10^4$ | $4 \times 19^4$ |
| 48 hrs | $8.0 \times 10^4$ | $5 \times 10^4$ | $6 \times 10^4$ | $6.5 \times 10^4$ |
| 72 hrs | $1.4 \times 10^5$ | $9 \times 10^4$ | $1 \times 10^5$ | $1.2 \times 10^5$ |
| Δ media |  |  |  |  |
| 96 hrs | $2.5 \times 10^5$ | $1.7 \times 10^5$ | $2 \times 10^5$ | $2.3 \times 10^5$ |
| 120 hrs | $3.5 \times 10^5$ | $2.8 \times 10^5$ | $3.4 \times 10^5$ | $3.5 \times 10^5$ |
| 144 hrs | $3.0 \times 10^5$ | $2.8 \times 10^5$ | $3.3 \times 10^5$ | $3.2 \times 10^5$ |
| Subcultured # | >10 | 10 | 50 | 50 |
| Saturation density cells/cm$^2$ | $3.5 \times 10^5$ | $2.8 \times 10^5$ | $3.4 \times 10^5$ | $3.5 \times 10^5$ |
| Doubling time (hrs) ave | 24 | 26 | 24 | 24 |
| Plating efficiency % | 10 | <1 | 10 | 0 |

(B) Propagation of Diploid Cell Lines with Finite Growth Potential

WI38 and Detroit 550 are ATCC certified human diploid cell lines with finite span. These lines were serially subcultured in Dulbecco's Modified Eagle's medium, pH 7.2, supplemented with 10% bovine serum (invention, 2 lots; Fetal Calf (Reheis ®), or Calf serum (KC Biol.)). The cultures were examined daily for qualitative growth changes. Growth parameters were taken at various passage numbers.

Results

Invention serum (both lots) performed superior to calf serum and just slightly inferior to fetal calf serum. The WI38 could be serially subcultured 60–65 times with the invention serum prior to crisis. (Crisis was demonstrated by appearance of granules within the cells; thin, stringy cells, lack of confluency rounded cells, inability to be subcultured.) Fetal serum promoted the cell line through 5–10 more passages whereas calf serum supported growth 20–25 passages less.

The Detroit 550 cell line reached crisis in FCS at 38, and in invention serum at 30–34. At this point the cells, after one week changing media everyday, transfering to smaller vessel, recovered but demonstrated a changed morphology from fibroblastic to epithelial-like. The cells in calf serum never recovered.

EXAMPLE 20

Propagation of WI38

TABLE 20

| | Pas-sage | FCS | CS | Invention Lot I | Invention Lot II |
|---|---|---|---|---|---|
| t-0 cell/cm$^2$ | 20 | $2 \times 10^4$ | $2 \times 10^4$ | $2 \times 10^4$ | $2 \times 10^4$ |
| 12 | 20 | $2 \times 10^4$ | $2.8 \times 10^4$ | $2.4 \times 10^4$ | $2.6 \times 10^4$ |
| 24 | 20 | $4.4 \times 10^4$ | $3 \times 10^4$ | $3.8 \times 10^4$ | $4.0 \times 10^4$ |
| 48 | 20 | $1.3 \times 10^4$ | $6.1 \times 10^4$ | $8.0 \times 10^4$ | $1.0 \times 10^5$ |
| 72 | 20 | $3 \times 10^5$ | $1.3 \times 10^5$ | $1.8 \times 10^5$ | $2.2 \times 10^5$ |
| Δ media | | | | | |
| 96 | 20 | $4.2 \times 10^5$ | $2.5 \times 10^5$ | $3.8 \times 10^5$ | $4 \times 10^5$ |
| 120 | 20 | $4.0 \times 10^5$ | $3.5 \times 10^5$ | $3.9 \times 10^5$ | $4 \times 10^5$ |
| Subculture # (received at 10) | | 70 | 40 | 60 | 65 |
| Saturation density | | $4 \times 10^5$ | $3.5 \times 10^5$ | $3.9 \times 10^5$ | $4 \times 10^5$ |
| Doubling time | | 20 | 24 | 22 | 22 |
| Plating efficiency % | | 30 | 15 | 20 | 25 |

EXAMPLE 21

Propagation of Detroit 550

TABLE 21

| | Pas-sage | FCS | CS | Invention Lot I | Invention Lot II |
|---|---|---|---|---|---|
| t-0 cells/cm$^2$ | 20 | $2 \times 10^4$ | $2 \times 10^4$ | $2 \times 10^4$ | $2 \times 10^4$ |
| 12 | 20 | $2.6 \times 10^4$ | $2.0 \times 10^4$ | $2.2 \times 10^4$ | $2.5 \times 10^4$ |
| 24 | 20 | $3.5 \times 10^4$ | $2.8 \times 10^4$ | $3 \times 10^4$ | $3.2 \times 10^4$ |
| 48 | 20 | $7.3 \times 10^4$ | $5 \times 10^4$ | $6.3 \times 10^4$ | $7.1 \times 10^4$ |
| 72 | 20 | $1.6 \times 10^5$ | $8 \times 10^4$ | $1.3 \times 10^5$ | $1.4 \times 10^5$ |
| Δ media | | | | | |
| 96 | 20 | $3 \times 10^5$ | $1.2 \times 10^5$ | $2.5 \times 10^5$ | $2.9 \times 10^5$ |
| 120 | 20 | $3.5 \times 10^5$ | $2.5 \times 10^5$ | $3.0 \times 10^5$ | $3 \times 10^5$ |
| 144 | 20 | $3 \times 10^5$ | $3 \times 10^5$ | $3.0 \times 10^5$ | $3 \times 10^5$ |
| Subculture #* (received at 9) | | 38 | 25 | 30 | 35 |
| Saturation density | | $3.5 \times 10^5$ | $3 \times 10^5$ | $3 \times 10^5$ | $3 \times 10^5$ |
| Doubling time (ave) hrs | | 24 | 35 | 28 | 26 |
| Plating efficiency % | | 10% | <1% | <1% | <1% |

*The Det 550 cell line underwent an altered morphology from fibroblasts-like to ephithelial-like; the subculture # reported here is the number of passages until this crisis period.

Example 22

Three separate cell fusions were performed using equal number of NS-1 cells (a mouse myeloma cell which is deficient in the production of HGPRT) grown in the appropriate type of bovine serum and splenic lymphocytes pooled from 3 Balb/c mice. The specific sera used were 2 lots of invention sera, and fetal bovine serum from Reheis ®. The cells were washed in serum free RPMI 1640 medium and fused in 1.5 ml of 50% PEG (polyethyleneglycol 4000 from Polysciences) for 2 minutes at 37°. Serum free media was then added to the fused cells at the rate of 0.2 ml/30 seconds until they were suspended to 10 mls. Serum free RPMI 1640 medium was then added to 50 mls and the cells gently pelleted. The cells were carefully resuspended in 25 mls of Iscoves modified Dulbecco's minimal essential media (Gibco) containing pyruvate, alphathioglycerol, transferrin, glutamine, hypoxanthine, thymine, and aminopterin (HAT media). HAT selection was carried out in Costar 96 well micro titre plates in a 37° CO$_2$ incubator. Clones of fused, aminopterin-resistant cells were visible within 3 weeks.

The fusion using invention serum lot #1 yielded only 4 colonies (out of 192 wells). Invention serum lot #2 yielded 56 colonies and Reheis ® fetal bovine serum gave 71 colonies (Table 22). The colonies grew out faster in the invention serum and were more diffuse.

These differences in fusion efficiency could easily be influenced by extremely small changes in the fusion conditions. In other experiments it had been found that small changes in the rate of dilution after fusion made large differences in the number of viable fused cells and in this experiment it was attempted to make the fusion protocals as similar as possible. Still, the rate of dilution remains a probable source of error in the experiment.

TABLE 22

| Sera | No. positive wells | % positive wells |
|---|---|---|
| Invention Lot I | 4 | 2.08% |
| Invention Lot II | 56 | 29.17% |
| Reheis ® FCS | 71 | 36.99% |

EXAMPLE 23

Replication of Retroviruses

This experiment is designed to compare the growth of reticuloendotheliosis associated virus (REV-A) an avian retrovirus, in cultures of chicken embryo fibroblasts grown in RPMI 1640 medium supplemented with 10% fetal calf serum or with 10% invention serum. The amount of REV-A produced at each time point was determined by assaying particle release by the reverse transcriptase activity.

Methods

Primary cultures of chicken embryo fibroblasts (CEF, SPAFAS, Norwalk, Conn.) were prepared from 9 day embryos. After 48 hours, cells of the primary cultures were trypsinized, washed from the plates and suspended in RPMI 1640 medium. Equal volumes containing $4.0$–$4.5 \times 10^6$ cells were added to each of 12 tissue culture flasks (75 cm$^2$). The remaining six flasks were given 12 ml of RPMI 1640 medium supplemented with 10% heat inactivated fetal calf serum (Reheis ®). After approximately 12 hours, the medium was removed from the flasks and replaced with RPMI 1640 medium containing polybrene (2µg/ml) supplemented with 1% of either invention serum or fetal calf serum. After 1 hour the cells in 10 flasks (5 with invention serum and 5 with fetal calf serum) were exposed to equal volumes of a stock to REV-a$_t$ previously obtained from secondary SPAFAS CEF cultures. the two remaining flasks were exposed to the same volume of medium containing polybrene alone and would serve as controls (C$_Z$ and C$_F$). Following a 1 hour adsorption period, the media in all flasks was replaced with fresh RPMI 1640 medium supplemented with either 10% invention serum or 10% fetal calf serum.

At various times after infection, the media was collected from each flask and replaced with appropriate fresh medium. The collected medium was centrifuged at 2,500 rpm for 15 minutes to remove cells and cellular debris. The virus in 10 ml of each sample was concentrated by centrifugation at $100,000 \times g$ for 1 hour. The resulting viral pellet was suspended in 0.2 ml of TT-2 buffer (0.05 M Tris, pH.3; 0.2% Triton X-100). The amount of virus in each sample was determined by assaying the amount of reverse transcriptase activity present in the concentrated virus sample. A standard exogenous reverse transcriptase reaction was carried out in a final volume of 0.1 ml containing 100 mM NaCl, 50 mM Tris-HCl (pH 8.3), 5 mM dithiothreitol (DTT), 0.05 M manganous acetate, 7.5 mM poly (rA), 1.9 μM oligo (dT) 12-18 0.2% Triton X-100 and 20 μCi of [$^3$H]-thymidine triphosphate; 40-60Ci/mM). Aliquots of 25 μL of the virus samples were added to 75 μl of the reaction mixture and incubated at 37° C. for 1 hour. All virus samples were assayed in duplicate. At the end of the incubation period, 2 ml of cold TP (0.4 M trichloroacetic acid, 0.02M sodium pyrophosphate) was added to each tube and the tubes were stored at 4° C. for 1 hour. The precipitate in each tube was collected on 0.45 m Millipore® filters, washed, dried and the amount of radioactivity determined using Bray's Scintillation Fluid and a Packard Tri-Carb Scintillation Counter.

Results

Figure 4:
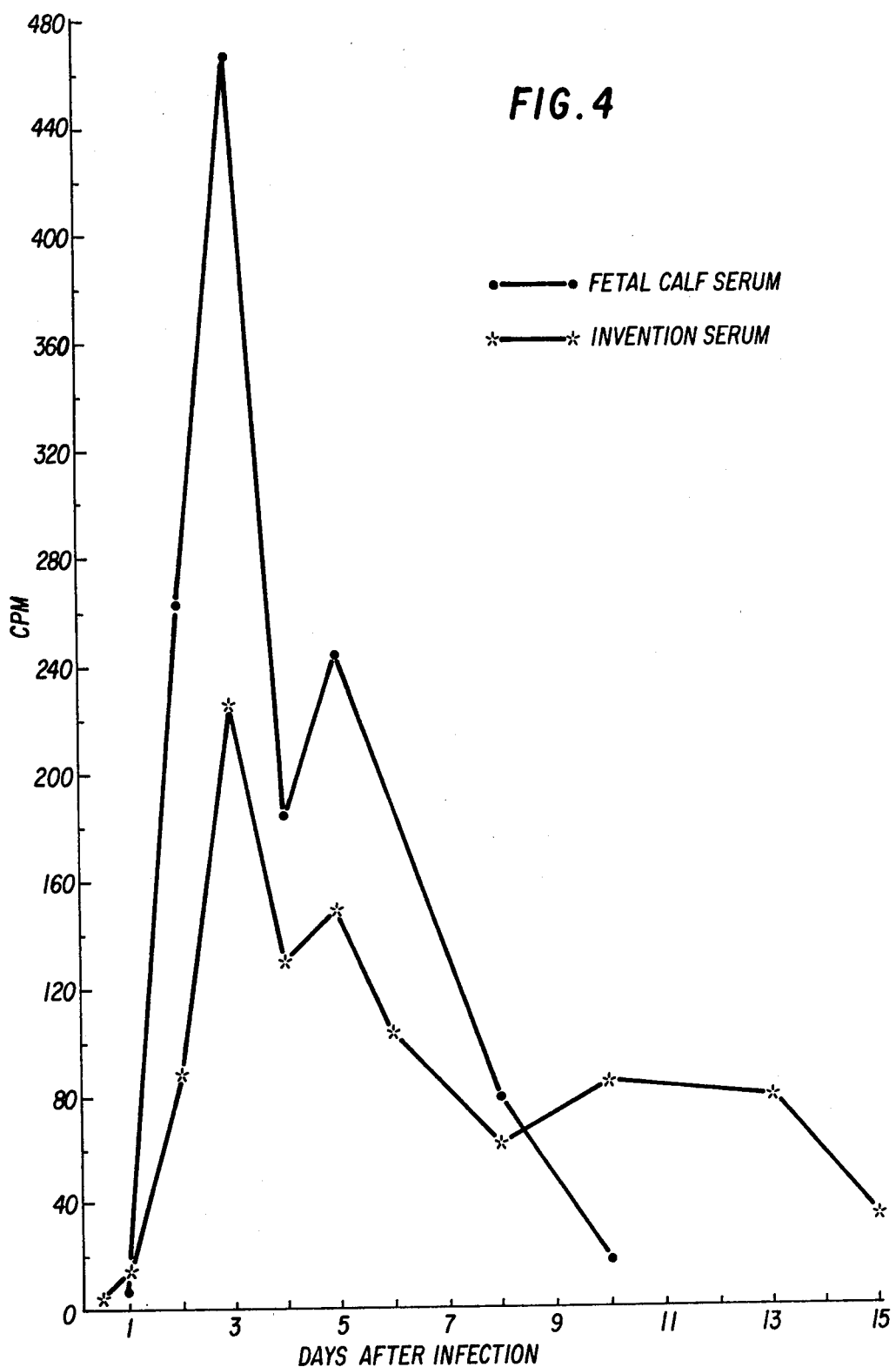
FIG. 4 compares the growth of REV-A virus in cultures of CEF grown in RPM1 1640 medium supplemented with 10% FCS and 10% Zeta Serum. See Example 23.

Table 23 summarizes the results by presenting the average of the duplicate RT-assays performed on each flask virus sample at each time point. Also presented is the average amount of RT activity produced by all 5 flasks at a given time point which is illustrated in FIG. 4.

TABLE 23

| FETAL CALF SERUM | | | INVENTION SERUM | |
|---|---|---|---|---|
| Average RT Activity per Flask (cts/min) | Average RT Activity (cts/min) | Flask | RT Activity per Flask (cts/min) | Average RT Activity (cts/min) |
| 3,896 | | A | 2,196 | |
| 2,541 | | B | 3,649 | |
| 2,049 | | C | 4,003 | |
| 3,317 | | D | 2,571 | |
| 2,922 | | E | 3,062 | |

TABLE 23-continued

| FETAL CALF SERUM | | | INVENTION SERUM | |
|---|---|---|---|---|
| Average RT Activity per Flask (cts/min) | Average RT Activity (cts/min) | Flask | RT Activity per Flask (cts/min) | Average RT Activity (cts/min) |
| | 2,945.0 | | | 3,870.5 |
| | 2,896.0 | $C_Z$ | | 2,949.5 |
| 10,410.5 | | A | 3,716 | |
| 6,128 | | B | 4,693 | |
| 6,520 | | C | 9,358 | |
| 5,299 | | D | 3,343.5 | |
| 3,808 | | E | 5,060.5 | |
| | 6,433.1 | | | 5,834.2 |
| | 2,567.0 | $C_Z$ | | 2,463 |
| 192,285 | | A | 34,446 | |
| 10,756.5 | | B | 103,689 | |
| 358,376 | | C | 57,627 | |
| 369,309 | | D | 70,967 | |
| 383,471 | | E | 14,200 | |
| | 262,869.5 | | | 38,185.7 |
| | 3,102 | $C_Z$ | | 3,001.5 |
| 476,457.5 | | A | 210,552 | |
| 348,718.5 | | B | 217,597 | |
| 569,562.5 | | C | 266,575.5 | |
| 425,807 | | D | 248,187 | |
| 512,295.5 | | E | 185,365 | |
| | 466,568.2 | | | 225,655.3 |
| | 2,341 | $C_Z$ | | 2,391 |
| 139,475 | | A | 188,493.5 | |
| 228,043 | | B | 156,176 | |
| 162,150 | | C | 120,569 | |
| 150,324 | | D | 35,696.5 | |
| 240,139.5 | | E | 18,372.5 | |
| | 184,026.3 | | | 129,861.5 |
| | 2,057 | $C_Z$ | | 2,172 |
| 274,053.5 | | A | 51,008.5 | |
| 319,019 | | B | 68,061 | |
| 304,283 | | C | 48,152.5 | |
| 205,337 | | D | 39,241 | |
| 119,894 | | E | 39,361.5 | |
| | 244,517.3 | | | 49,164.9 |
| | 3,607 | $C_Z$ | | 2,943 |

| | | FETAL CALF SERUM | | INVENTION SERUM | |
|---|---|---|---|---|---|
| Time after Infection | Flask | Average RT Activity per Flask (cts/min) | Average RT Activity (cts/min) | Flask | RT Activity per Flask (cts/min) | Average RT Activity (cts/min) |
| 144 hrs (6d) | A | 189,611 | | A | 112,593.5 | |
| | B | 126,323.5 | | B | 37,203 | |
| | C | 209,345 | | C | 31,142 | |
| | D | 118,608 | | D | 56,423 | |
| | E | 310,971 | | E | 35,801.5 | |
| | | | 190,971.9 | | | 12,593.5 |
| | $C_F$ | | 2,802 | $C_Z$ | | 2,897 |
| 192 hrs (8a) | A | 37,968.5 | | A | 44,941.5 | |
| | B | 226,438 | | B | 75,075 | |
| | C | 75,444 | | C | 43,483 | |
| | D | 41,353 | | D | 56,859 | |
| | E | 16,368.5 | | E | 36,212 | |
| | | | 79,514.4 | | | 51,314.1 |
| | $C_F$ | | 2,415.5 | $C_Z$ | | 2,951.5 |
| 240 hrs (10a) | A | 19,957.5 | | A | 79,524 | |
| | B | 21,066 | | B | 102,708 | |
| | C | 18,954 | | C | 56,262 | |
| | D | 19,856.5 | | D | 12,955 | |
| | E | 7,293 | | E | 18,366 | |
| | | | 17,491.5 | | | 35,963 |
| | $C_F$ | | 2,207 | $C_Z$ | | 2,264 |
| 312 hrs (13d) | A | — | | A | 95,506.5 | |
| | B | — | | B | 34,739.5 | |
| | C | — | | C | 95,504 | |
| | D | — | | D | 70,419 | |
| | E | — | | E | 95,927 | |
| | | | | | | 80,419.1 |
| | | | | $C_Z$ | | 2,444.5 |
| 360 hrs (15d) | A | — | | A | 20,513 | |
| | B | — | | B | 76,159 | |

-continued

| Time after Infection | FETAL CALF SERUM | | | INVENTION SERUM | | |
|---|---|---|---|---|---|---|
| | Flask | Average RT Activity per Flask (cts/min) | Average RT Activity (cts/min) | Flask | RT Activity per Flask (cts/min) | Average RT Activity (cts/min) |
| | C | — | | | 39,515 | |
| | D | — | | | 15,602 | |
| | E | — | | | 18,961 | |
| | | | | | | 34,150 |
| | | | | $C_Z$ | 2,583 | |

It appears that cultures grown in the presence of 10% fetal calf serum more rapidly developed a confluent monolayer. This more rapid growth of the cells in these cultures resulted in the monolayers beginning to dissassociate from flask beginning 5 days after infection, with virtually the entire monolayer removed after 5 days. However the cultures grown in the presence of fetal calf serum produced what appears to be twice as much REV-A at the peak of viral production 3 days after infection than identical cultures grown in the presence of invention serum. The relatively rapid decline in REV-A production appears to be correlated with the confluence culture monolayer dissassociating from the substratum. Cultures grown in media supplemented with invention serum did not display the rather rapid growth, like the culture grown in the presence of fetal calf serum. The cultures grown in invention serum did not begin to lift off until about 14 days after infection. Though the peak viral production in the presence of invention serum is about half that of fetal calf serum cultures, the cultures continue to produce virus about 3× longer, reflecting the differences in growth rates of the 2 types of cultures. Invention serum allows CEF cultures to grow at a slower rate than fetal calf serum, resulting in the cultures producing virus for a greater period of time.

EXAMPLE 24

Mitogen Stimulation of Mouse Lymphocytes

Fetal calf serum (KC Biologicals) was compared to invention serum with regard to effect on stimulation of mouse spleen cells by mitogen.

Spleens were removed from three 4–5 month old mice and mashed through fine mesh screens with a syringe tip into RPMI 1640 medium. The cells were pelleted at 1200 rpm for 10 minutes, divided into six tubes, counted and washed again. The appropriate serum type and amount was added to each tube (in RPMI 1640), and the cells were dispensed in 0.5 ml per 12×75 mm tube. PHA (Difco) was added to quadruplicate cultures (0.1 ml per tube of a 1:80 dilution); duplicate control cultures were used.

The cultures were incubated for 48 hours at 37° C., then pulsed for 24 hours with tritiated thymidine (1 mCi/tube in 0.05 ml media). The cells were vortexed and poured on fiberglass filters. The tubes were washed twice with TCA, and the filters were then counted in the scintillation counter.

Two concentrations of serum (5% and 10%) and two concentrations of cells (2×10$^6$/ml and 5×10$^5$/ml) were tested.

Results are shown in Table 24

TABLE 24

| | +PHA | −PHA | STIM. INDEX |
|---|---|---|---|
| 1. 5 × 10$^5$ cells | | | |
| A. 5% | | | |
| FCS | 2005 ± 1174 | 682 ± 86 | 2.9 |
| Invention Lot #1 | 2157 ± 872 | 2139 ± 135 | 1 |
| Invention Lot #2 | 3801 ± 898 | 688 ± 84 | 5.5 |
| B. 10% | | | |
| FCS | 12,752 ± 3676 | 2115 ± 117 | 6.0 |
| Lot #1 | 4518 ± 483 | 646 ± 55 | 6.99 |
| Lot #2 | 3348 ± 405 | 1789 ± 528 | 1.9 |
| 2. 2 × 10$^6$ cells | | | |
| A. 5% | | | |
| FCS | 7369 ± 1816 | 1279 ± 166 | 5.8 |
| Lot #1 | 56,905 ± 2729 | 8802 ± 1821 | 6.5 |
| Lot #2 | 6898 ± 595 | 1567 ± 248 | 4.4 |
| B. 10% | | | |
| FCS | 32,093 ± 2990 | 5203 ± 205 | 6.2 |
| Lot #1 | 8147 ± 3143 | 1379 ± 225 | 5.9 |
| Lot #2 | 13,428 ± 701 | 1601 ± 65 | 8.4 |

Stim. Index + $\frac{+PHA}{-PHA}$

Conclusion

Invention serum is as good as fetal calf serum in enhancing stimulation of mouse cells by PHA.

EXAMPLE 25

Analysis of DNA Synthesis in Polyclonally Activated Lymphocytes Stimulated by Concanavalin A DNA synthesis was monitored by $^3$H-thymidine (1 µCi/ml) incorporation after Con A stimulation. Control cultures contained 5% regular fetal calf serum (Microbiological Associates). Cultures designated "Zeta" contained 5% invention serum (Example 1). Each set consists of 5 cultures.

| | 48 hr values DPM/10$^6$ cells/hour | | |
|---|---|---|---|
| | mean | | standard error |
| Control | 150872 | ± | 8496 |
| Invention Serum | 128361 | ± | 7236 |

Figure 5:
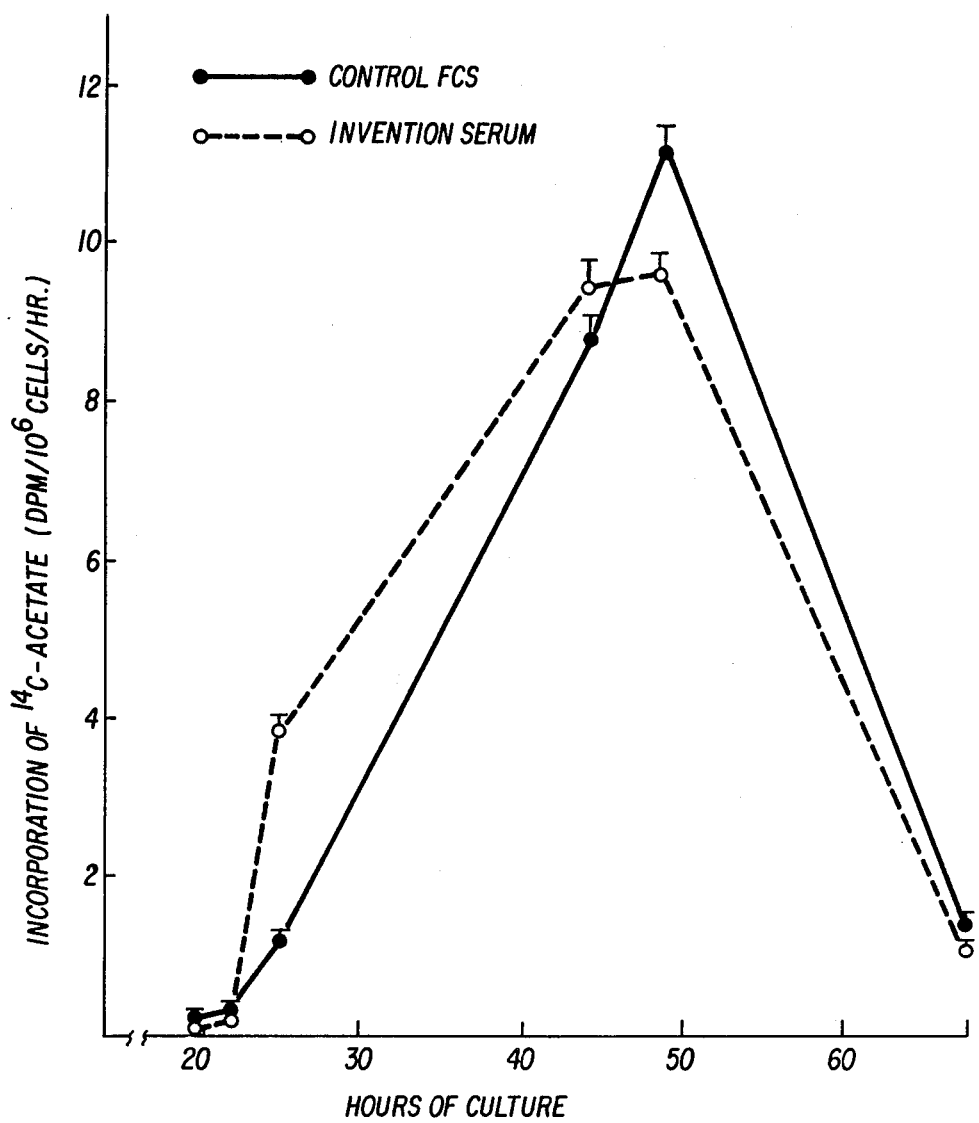
FIG. 5 compares DNA synthesis in polyclonally activated lymphocytes stimulated by concanavalin A in FCS and Zeta Serum. See Example 25.

The kinetics of the DNA synthesis are depicted in FIG. 5.

EXAMPLE 26

Synthesis of Cholesterol in Polyclonally Activated Mouse Lymphocytes

Sterol synthesis was measured by $^{14}$C-acetate incorporation into the digitonin precipitate of the nonsaponificable lipid fraction.

| | DPM/10⁶ cells/hour |
|---|---|
| Control | 241 ± 8 |
| Invention Serum | 1519 ± 224 |

Figure 6:
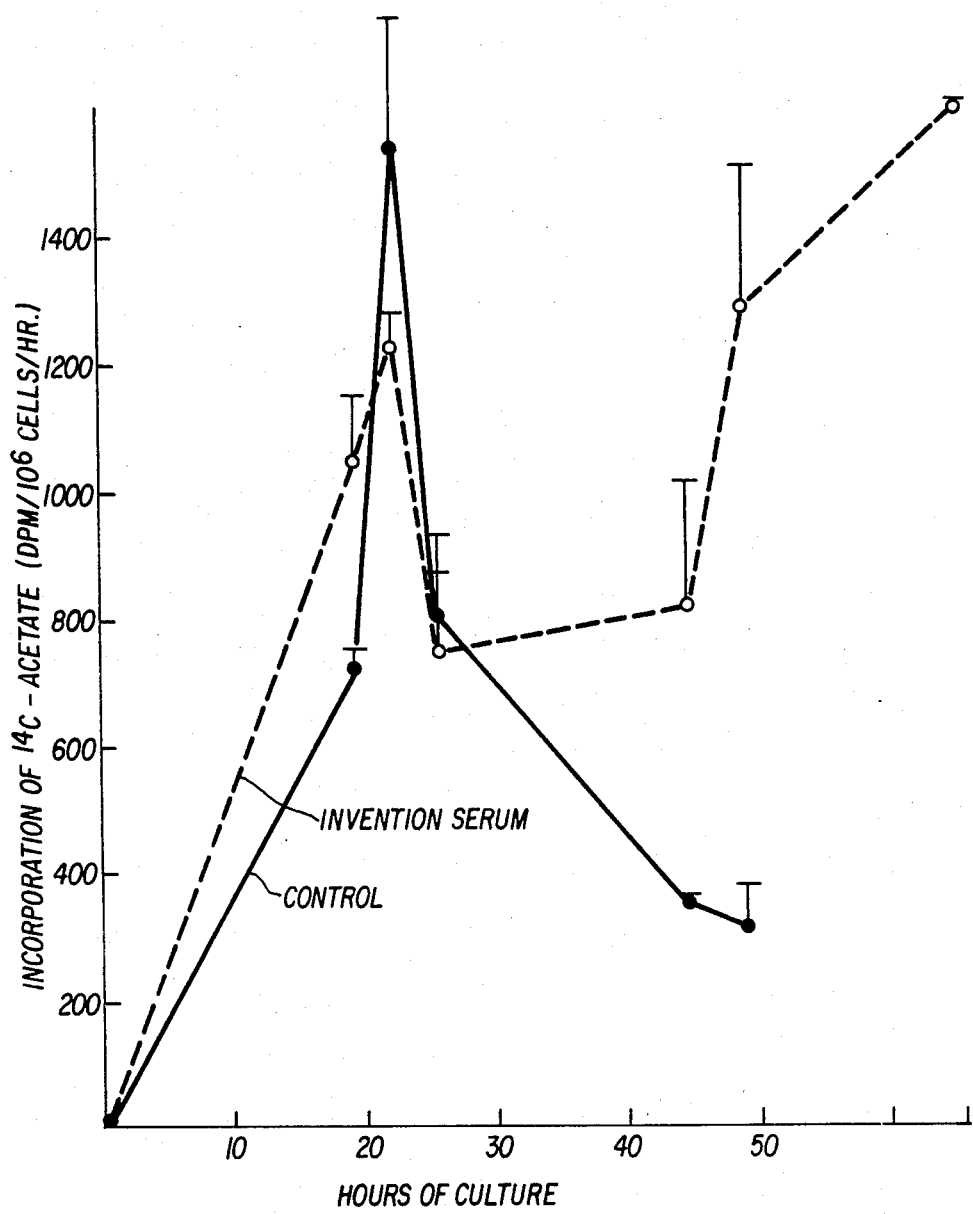
FIG. 6 compares cholesterol synthesis in polyclonally activated lymphocytes, in FCS and Zeta Serum. See Example 26.

FIG. 6 depicts the time course of sterol synthesis in such cultures. Each point represents 3 cultures. Note the second peak of sterol synthesis in Invention serum which indicates the probable beginning of a second cell cycle.

EXAMPLE 27

Cytotoxic titers in polyclonally activated lymphocytes

Figure 7:
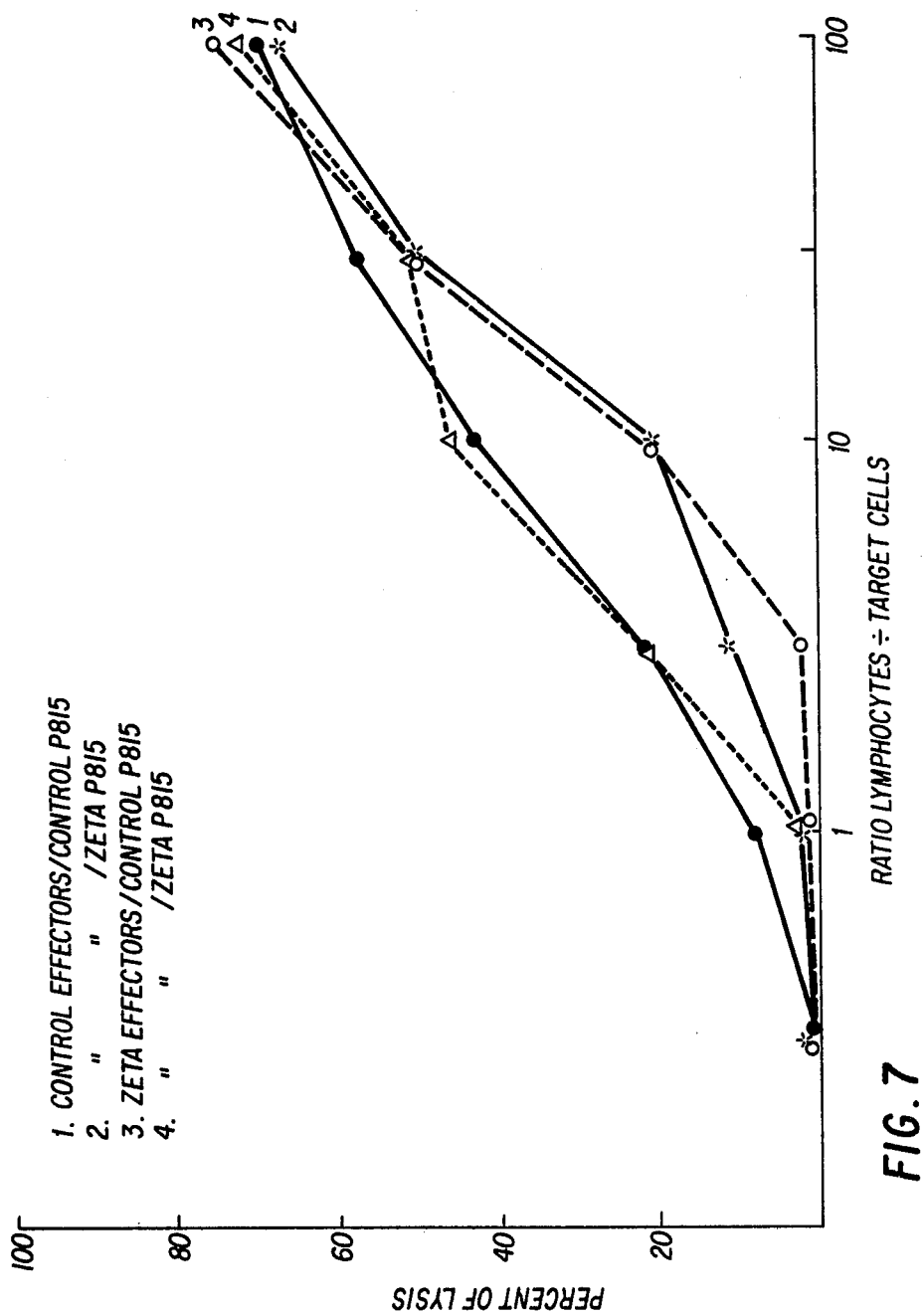
FIG. 7 compares cytotoxic titers in polyclonally activated lymphocytes in FCS and Zeta Serum. See Example 27.

Cytotoxic titers were determined at 48 hr using $^{51}$Cr labeled P815 target cells (mastocytoma). Effector cells (lymphocytes) or target cells were cultured in control serum (FCS) or invention sera respectively as indicated in FIG. 7.

Figure 8:
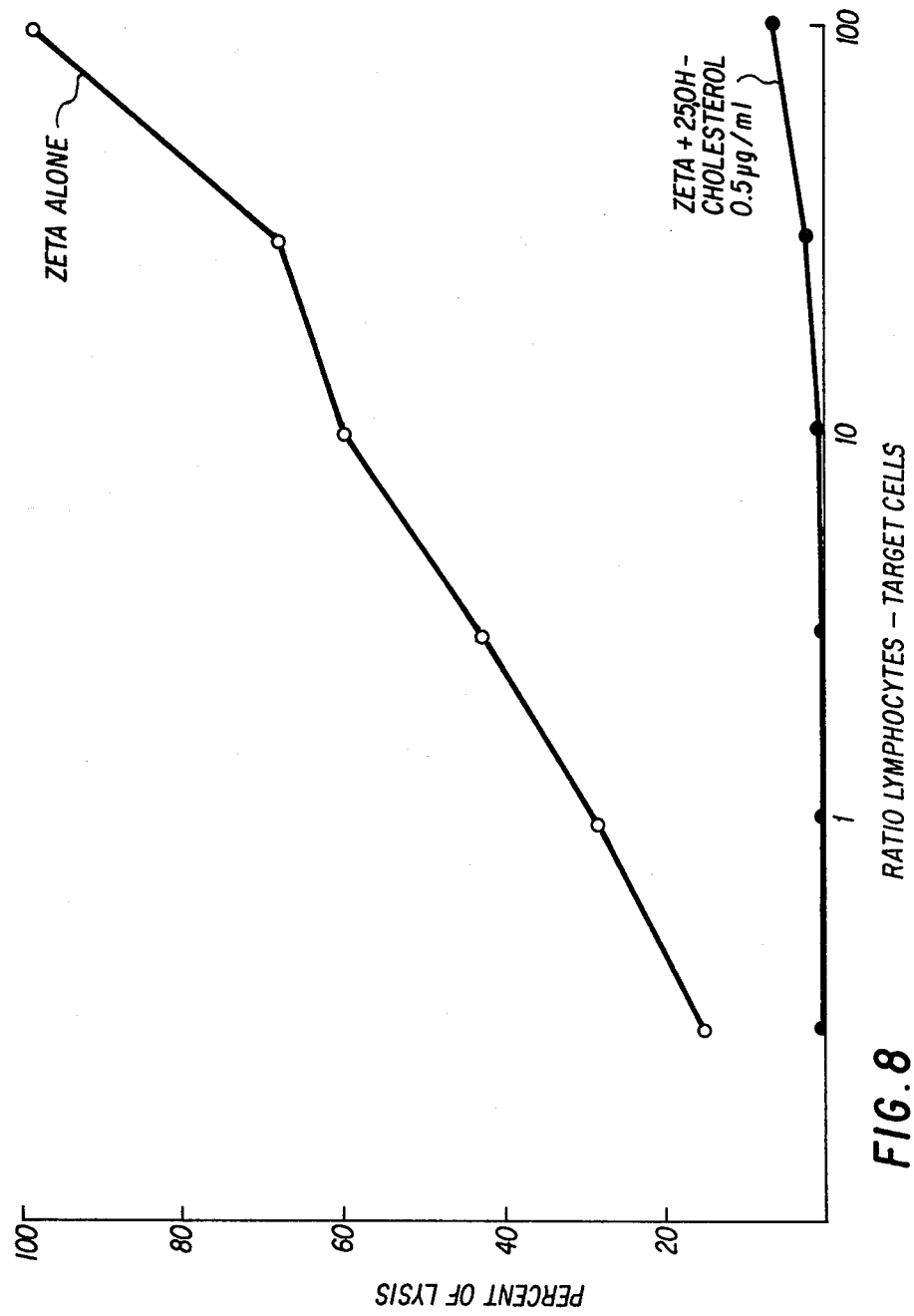
FIG. 8 compares cytotoxic titers in invention serum with or without addition of 25-OH-cholesterol. See Example 27.

FIG. 8 shows cytotoxic titers in a different lot of invention serum with and without addition of the sterol synthesis inhibitor 25-OH-Cholesterol.

Figure 9:
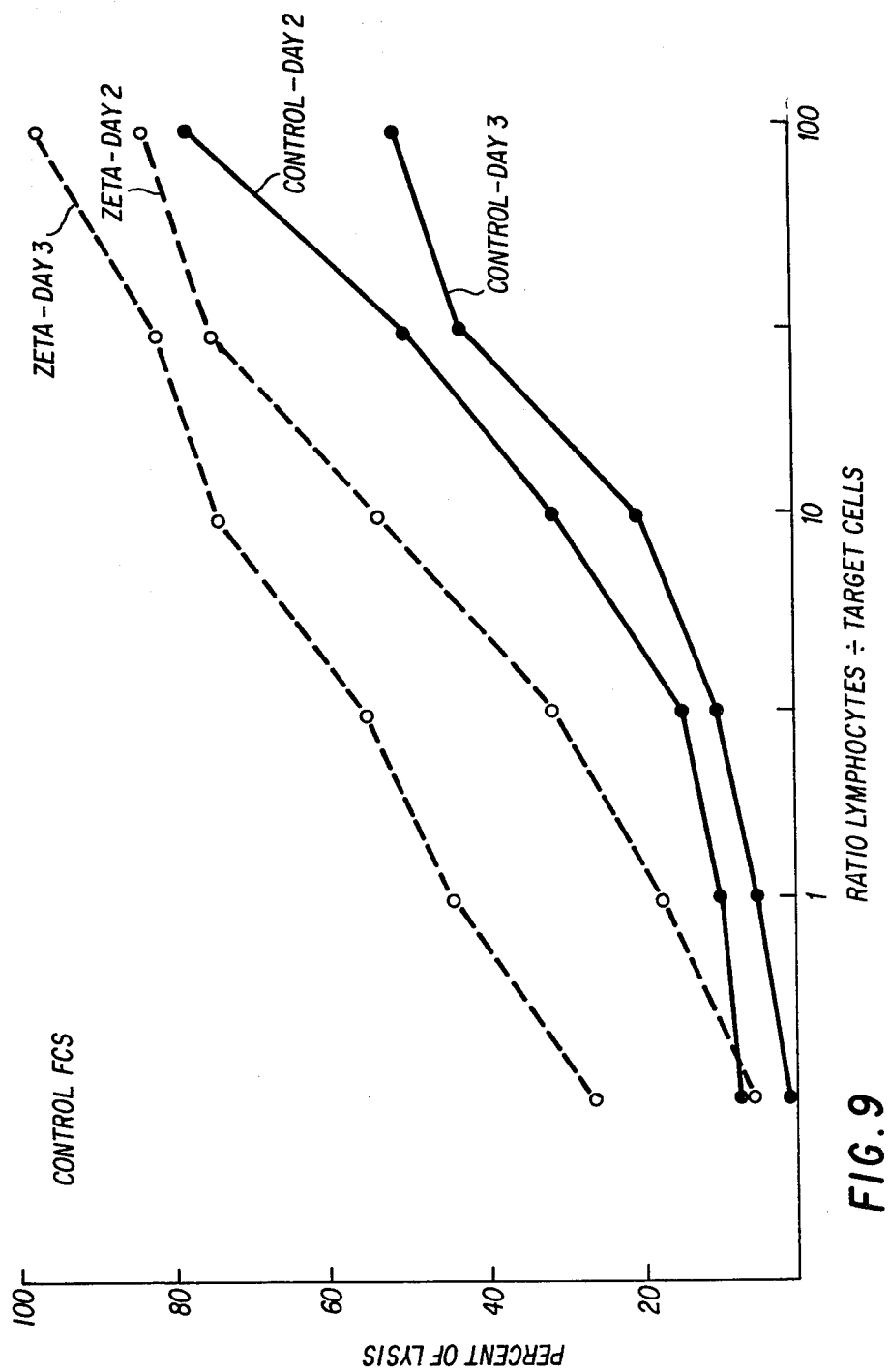
FIG. 9 compares cytotoxic titers in polyclonally activated lymphocytes in FCS and Zeta Serum. See Example 27.

FIG. 9 depicts the cytotoxic titers in another experimental series measured at 48 hr and 72 hr after Con A stimulation. Clearly, invention sera resulted in better cytotoxic titers than those obtained in regular fetal calf serum.

EXAMPLE 28

Synthesis of Cholesterol in P815 Macrocytoma Cells

The cultures were incubated for 2 hrs with $^{14}$C-acetate (5 μCi/ml) at 37° and the lipids then extracted, fractionated and the radioactivity was measured in the digitonin-precipitable fraction.

| | DPMA/10⁶ cells/hour |
|---|---|
| Control (5% FCS) | 16260 ± 2732 |
| Invention serum | 25493 ± 3931 |

The higher sterol synthesis in the Invention serum may be attributable to a lower cholesterol content in this serum.

EXAMPLE 29

Synthesis of DNA in P815 Macrocytoma Cells

The cells were incubatd with 3H-TdR (1 μcl/ml) for 1 hr at 37° C. and the radioactivity determined in the acid-insoluble fraction.

| | DPM/10⁶ cells/hour |
|---|---|
| Control (5% FCS) | 206350 ± 17808 |
| Invention serum 5% | 204698 ± 10988 |

EXAMPLE 30

Induction of Differentiation in DS19 Erythroleukemia Cells

Figure 10:
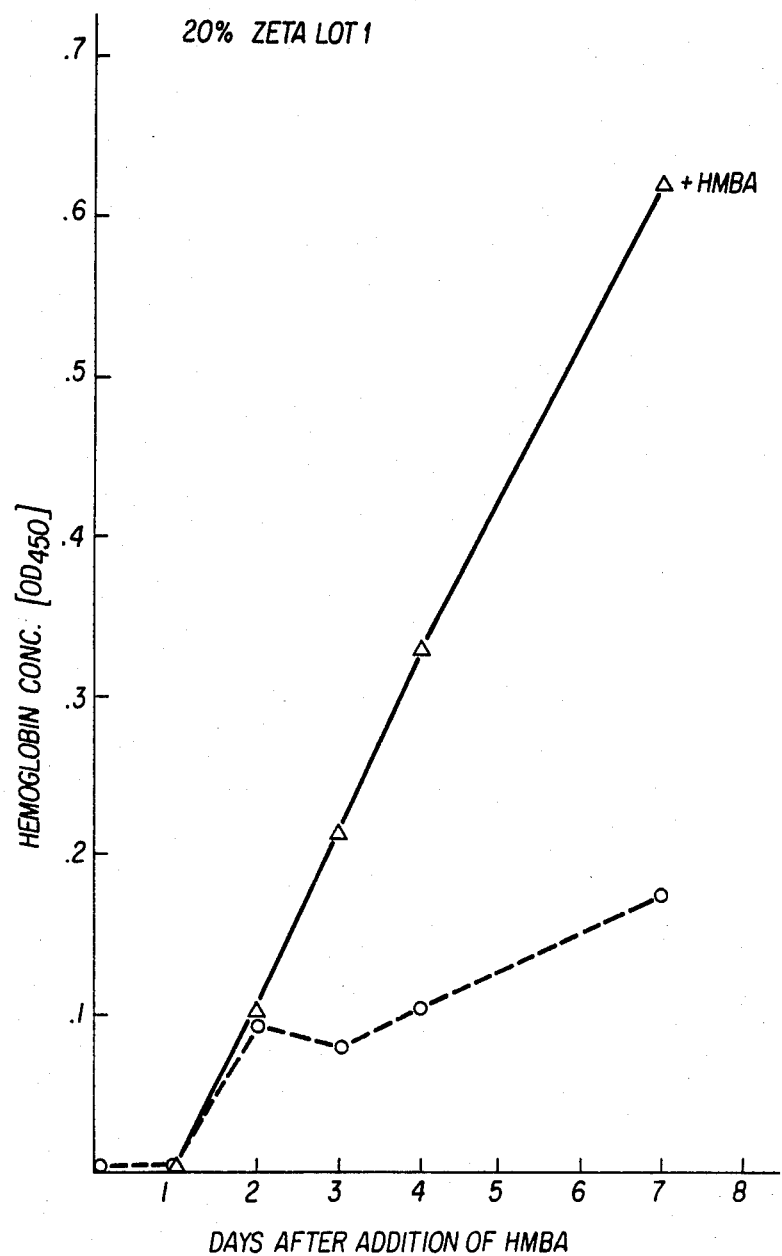
FIGS. 10 and 11 compare the induction of differentiation in DS19 erythroleukemia cells by hexamethylene-bis-acetamide (HMBA) in Zeta Serum with and without HMBA. See Example 30.
Figure 11:
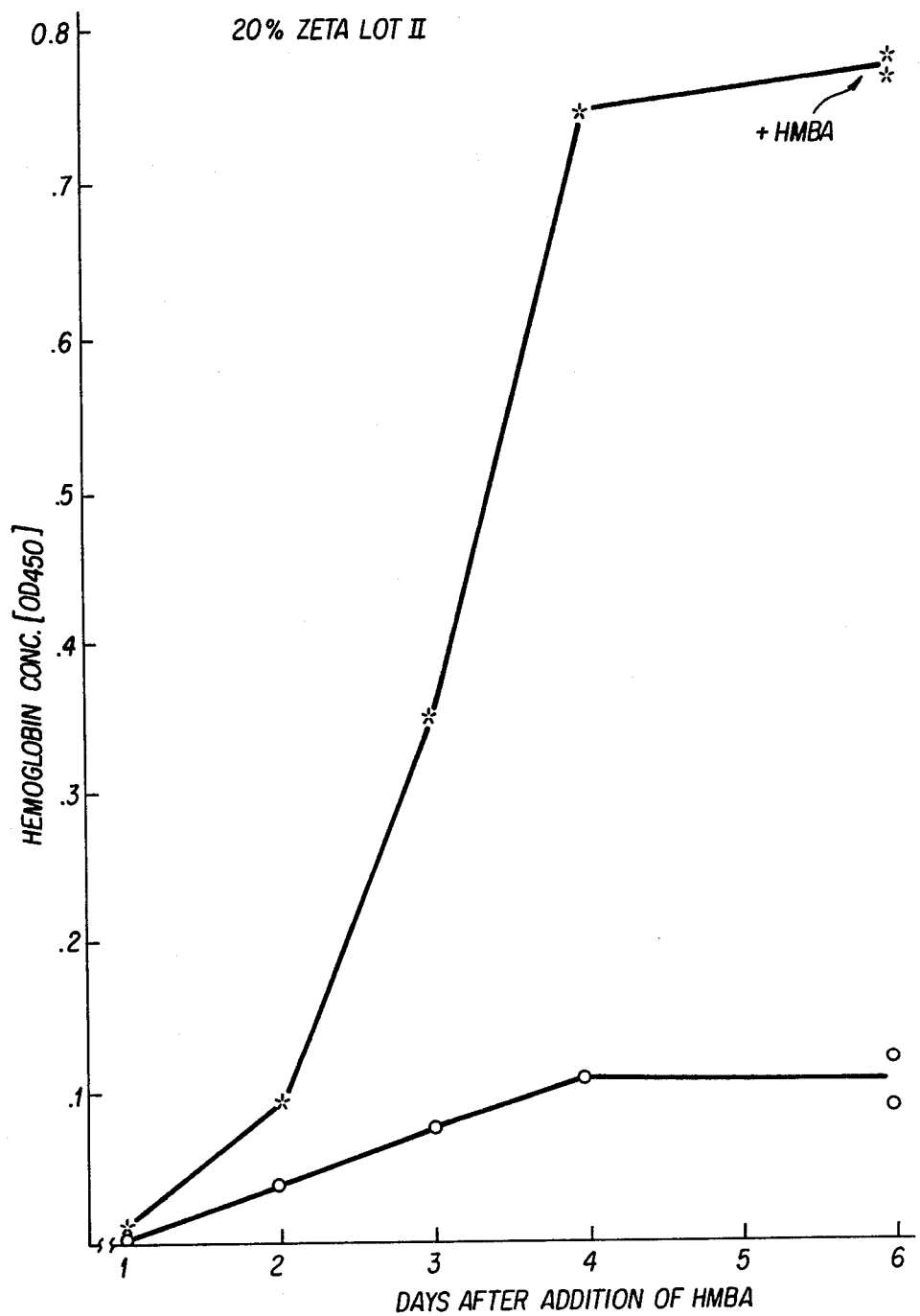

The DS19 erythroleukemia cell line is transformed by Friend leukemia virus and has the interesting capability to differentiate into hemoglobin producing cells if certain chemicals (inducers) are added to the culture medium. One of the most powerful inducers is hexamethylene-bis-acetamide (HMBA). Two experiments were conducted involving two lots of invention serum. In FIGS. 10 and 11, the results of these experiments are depicted for both lots, respectively. Controls are cultures which are grown in invention serum without differentiation inducers, they proliferate but do not produce hemoglobin. Cultures to which HMBA has been added (+HMBA) produce significant amounts of hemoglobin. These results are equal or even better as compared to cultures grown in regular fetal calf serum (not depicted).

Conclusions about Experiments 25–30

For the three cell types tested, (polyclonally activated lymphocytes, P815 macrocytoma and FLV erythroleukemia) these cell lines grow at least equally as well or even better in invention serum compared to fetal calf serum under all conditions.

Having now fully described this invention, it will be apparent to one of ordinary skill in the art that the details of formulation or operation thereof can be subject to changes without departing from the spirit of the invention or any embodiments thereof.

What is claimed as new and intended to be covered by Letters Patent of the United States is:

1. A medium derived from an admixture of 1–99% natural fetal calf serum, and 99–1% of natural bovine serum which comprises less than 30 mg/dl of total lipids; cholesterol levels within 0–10 mg/dl; triglyceride levels within 0–20 mg/dl; albumin and beta globulin levels substantially similar to those of fetal bovine serum; alpha-globulin levels lower than or similar to that of fetal bovine serum; gamma-globulin up to 1.0 g/dl: hemoglobin levels less than 20 mg/dl; mycoplasma levels and eveloped virus levels being substantially undetectable.

2. A serum composition comprising
(a) a serum derived from natural bovine serum (B.S.) which comprises less than 30 mg/dl of total lipids; cholesterol levels within 0–10 mg/dl; triglyceride levels within 0–20 mg/dl; hemoglobin levels less than 20 mg/dl; mycoplasma levels and enveloped virus levels being substantially undetectable and;
(b) a natural fetal calf serum (FCS), wherein said FCS is present in 1–99% of said combination, and said B.S. derived serum if present in 99–1% of said composition.

3. The serum composition of claim 2 wherein prior to said combination, said B.S. derived serum (a) contains albumin, - globulin and - glubulin levels similar to those of fetal calf serum.

4. The serum composition of claim 2, wherein prior to said combination said B.S. derived serum (a) has albumin levels within 2–4 g/dl, alpha globulin levels within 0.4–2.0 g/dl, and beta globulin levels within 0.4–2.0 g/dl.

5. A tissue culture medium comprising the serum of any of claims 2, 3, or 4.

6. The serum composition of claim 2, 3 or 4 wherein prior to said combination, said B.S. derived serum (a) has gamma-globulin levels within 0.0–1.0 g/dl and endotoxin levels less than 2.0 ng/ml.

7. The serum composition of claim 2, 3 or 4 wherein prior to said combination, said B.S. derived serum (a) has cortisol levels less than 5 g/ml.

8. The serum composition of claim 2, 3 or 4 wherein prior to said combination, said B.S. derived serum (a) has (a) gamma-globulin levels within 0.1–1.0 g/dl; (b) cortisol levels less than 5 g/ml; and (c) endotoxin levels less than 2.0 ng/ml.

9. The serum composition of claims 2 or 3 wherein prior to said combination said B.S. derived serum (a) has gamma-globulin levels within 0.0-0.5 g/dl.

10. The serum composition of claim 2 wherein said fetal calf serum is present at 5-10% by volume of said combination.

11. An in vitro cell culture comprising animal or plant cells together with the serum of claim 2.

12. The cell culture of claim 11 wherein said serum is present in growth promoting amounts.

13. The cell culture of claim 12 wherein said cells are transformed or non-transformed animal cells.

14. The cell culture of claim 12 wherein said cells are hybridomas.

15. The cell culture of claim 11 wherein said fetal calf serum if present at 5-10% by volume of said combination.

16. A method of culturing animal or plant cells in vitro which comprises contacting said cells with a growth promoting amount of the serum of claim 2.

17. The method of claim 16 wherein said fetal calf serum is present at 5-10% by volume of said combination.

18. The method of claim 16 wherein said cells are or are derived from lymphocytes or leukocytes.

19. The method of claim 16 wherein said cells are used for the production of viruses.

20. A process for the preparation of a serum which comprises
   (a) delipidizing natural bovine serum to a concentration of lipids less than 30 mg/dl,
   (b) precipitating proteins with ammonium sulfate to concentrations of alubumin and $\beta$-globulin substantially similar to those of fetal bovine serum, a concentration of $\alpha$-globulin lower than or similar to that of fetal bovine serum and to $\gamma$-globulin levels of up to 1.0 g/dl; and
   (c) admixing 99-1% of the serum obtained from steps (a) and (b) with 1-99% of natural fetal calf serum.

21. The process of claim 20 wherein said delipidization treatment is carried out by contacting said serum with fumed silica.

22. The process of claim 21 wherein said fumed silica is added batchwise to said serum to about 10-100 g/l.

23. The process of claim 21 wherein said fumed silica is immobilized in a fibrous matrix.

24. The process of claim 21 wherein prior to the contact with said silica, said serum is treated with a divalent metal ion to a concentration of 0.01-0.5 M.

25. The process of claim 20 which further comprises contacting said serum with activated charcoal.

26. The process of any of claims 24 or 25 wherein said divalent metal ion is calcium ion.

27. The process of any of claims 20 or 25 which further comprises separating precipitated protein from the supernatant, recovering the supernatant and substantially decreasing the concentration of dissolved salt remaining therein.

28. The process of claim 20 which comprises
   (a) adding a divalent metal ion to said serum to a concentration of 0.01-0.5M; then
   (b) contacting said serum with fumed silica for a time sufficient to bring the total lipid concentration to less than 30 mg/dl; then
   (c) separating said silica from said serum;
   (d) precipitating globulins from said serum with 20-35% ammonium sulfate, then
   (e) separating said precipitated protein from the supernatant and substantially decreasing the concentration of dissolved precipitating salt remaining in said supernatant; then
   (f) contacting said substantially salt-free supernatant with activated charcoal; separating said serum from said charcoal to obtain a clarified serum; then
   (g) adjusting the protein concentration in said clarified serum to a range of 3-7 g/dl; and then
   (h) heat inactivating said serum.

29. The process of claim 28 which further comprises sterilizing said serum after step (h).

30. The serum prepared by the process of claim 28.

31. The serum prepared by the process of claim 20.

32. A method of enhancing the cell growth promoting ability of natural bovine serum which comprises treating said serum by the process of claim 20.

* * * * *